United States Patent
Dinh et al.

(10) Patent No.: US 12,215,114 B2
(45) Date of Patent: Feb. 4, 2025

(54) PROCESSES AND INTERMEDIATES FOR PRODUCING DIAZASPIRO LACTAM COMPOUNDS

(71) Applicant: NAUREX INC., Madison, NJ (US)

(72) Inventors: Danny T. Dinh, Costa Mesa, CA (US); William R. Perrault, Kalamazoo, MI (US); Khalid Diker, Saint Leu D'esserent (FR)

(73) Assignee: NAUREX INC., Madison, NJ (US)

( * ) Notice: Subject to any disclaimer, the term of this patent is extended or adjusted under 35 U.S.C. 154(b) by 621 days.

(21) Appl. No.: 17/621,905

(22) PCT Filed: Jun. 23, 2020

(86) PCT No.: PCT/US2020/039164
§ 371 (c)(1),
(2) Date: Dec. 22, 2021

(87) PCT Pub. No.: WO2020/263848
PCT Pub. Date: Dec. 30, 2020

(65) Prior Publication Data
US 2022/0259217 A1    Aug. 18, 2022

Related U.S. Application Data

(60) Provisional application No. 62/865,840, filed on Jun. 24, 2019.

(51) Int. Cl.
*C07D 487/10* (2006.01)
*C07D 207/16* (2006.01)
*C07D 498/04* (2006.01)

(52) U.S. Cl.
CPC ......... *C07D 487/10* (2013.01); *C07D 207/16* (2013.01); *C07D 498/04* (2013.01)

(58) Field of Classification Search
CPC ... C07D 487/10; C07D 207/16; C07D 498/04
See application file for complete search history.

(56) References Cited

U.S. PATENT DOCUMENTS

| 5,688,787 A | 11/1997 | Burnett et al. |
| 9,512,134 B2 | 12/2016 | Lowe, III et al. |
| 2015/0336969 A1 | 11/2015 | Khan et al. |
| 2017/0231956 A1* | 8/2017 | Lowe, III ................ A61P 25/20 514/210.02 |

FOREIGN PATENT DOCUMENTS

| WO | WO-2014120783 A1 | 8/2014 |
| WO | WO-2014120786 A1 | 8/2014 |
| WO | WO-2017201283 A1 | 11/2017 |
| WO | WO-2017201285 A1 | 11/2017 |
| WO | WO-2019152696 A1 | 8/2019 |
| WO | WO-2020263847 A1 | 12/2020 |
| WO | WO-2020263848 A1 | 12/2020 |

OTHER PUBLICATIONS

PCT/US2020/039164 International Search Report and Written Opinion dated Nov. 9, 2020.

\* cited by examiner

*Primary Examiner* — Timothy R Rozof
(74) *Attorney, Agent, or Firm* — Wilson Sonsini Goodrich & Rosati

(57) ABSTRACT

Processes for producing diazaspiro lactam compounds and intermediates useful in the processes.

20 Claims, No Drawings

PROCESSES AND INTERMEDIATES FOR PRODUCING DIAZASPIRO LACTAM COMPOUNDS

CROSS-REFERENCE TO RELATED APPLICATIONS

This application claims priority to and/or the benefit of U.S. provisional application 62/865,840 filed Jun. 24, 2019 which is hereby incorporated by reference in its entirety and serves as the basis of a priority and/or benefit claim for the present application.

TECHNICAL FIELD

The subject matter described herein relates to processes for producing diazaspiro lactam compounds and intermediates useful in the processes.

BACKGROUND

N-methyl-D-aspartate receptor (NMDA receptor) is believed to play a major role in the synaptic plasticity that underlies many higher cognitive functions, such as memory acquisition, retention and learning, as well as in certain cognitive pathways and in the perception of pain. The NMDA receptor also appears to be involved in a broad spectrum of CNS disorders. NMDA receptor modulators therefore can provide pharmaceutical benefits.

U.S. Pat. No. 9,512,134, which is incorporated herein by reference in its entirety, discloses NMDA receptor modulators that can be useful for treating, for example, depression. There remains a need for economical and facile processes for the preparation of the diazaspiro lactam compounds described herein.

BRIEF SUMMARY

The following aspects and embodiments thereof described and illustrated below are meant to be exemplary and illustrative, not limiting in scope.

In one aspect, a process of producing a compound of formula I or a pharmaceutically acceptable salt thereof is provided. The process comprises contacting a compound of formula II and a coupling agent in an organic solvent to obtain a compound of formula I or a pharmaceutically acceptable salt thereof:

[formula II structure] → Coupling Agent / Organic Solvent → [formula I structure]

wherein:

$R_b$ is selected from H, halogen, cyano and $C_1$-$C_6$ alkyl;

$R_1$ is H or $C_1$-$C_6$ alkyl;

$R_2$ is H or $C_1$-$C_6$ alkyl;

$R_3$ is selected from $C_1$-$C_6$ alkyl and $C(O)OR_8$;

$R_8$ is selected from $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, and —$CH_2$—$C_3$-$C_{10}$ cycloalkyl, wherein $C_3$-$C_{10}$ cycloalkyl is optionally substituted with one, two, or three groups selected from $C_1$-$C_3$ alkyl;

$R_4$ and $R_5$ are independently selected from H, $C_1$-$C_6$ alkyl, X, and —$C_1$-$C_6$ alkylene-X, wherein X is selected from:

(i) $C_3$-$C_6$ cycloalkyl;

(ii) heteroaryl including from 5 to 6 ring atoms wherein one, two, or three of the ring atoms are independently selected from N, NH, N($C_1$-$C_3$ alkyl), O, and S;

(iii) heterocyclyl including from three to six ring atoms wherein 1, 2, or 3 of the ring atoms are independently selected from N, NH, N($C_1$-$C_3$alkyl), O, and S; and (iv) phenyl;

wherein $C_3$-$C_6$ cycloalkyl, heterocyclyl, heteroaryl, and phenyl are each optionally substituted with one, two, or three substituents independently selected halogen, cyano, $C_1$-$C_6$ alkyl, hydroxyl, and $C_1$-$C_6$ alkoxy;

or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from —N—$C_1$-$C_6$ alkyl, O and S; and wherein the heterocyclyl is optionally substituted with one, two, or three substituents independently selected from halogen, cyano, $C_1$-$C_6$ alkyl, and $C_1$-$C_6$ alkoxy;

$R_6$ is selected from —OH, $C_1$-$C_6$ alkoxy, —OC(O)—$C_1$-$C_6$ alkyl, and —OC(O)phenyl; and $R_7$ is H or $C_1$-$C_6$ alkyl.

In another aspect, a compound that is useful in the process of producing the diazaspiro lactam compound of formula I is provided. The compound is a compound of formula II:

[formula II structure]

wherein $R_b$, $R_1$, $R_2$, $R_3$, $R_4$, $R_5$, $R_6$, and $R_7$ are the same as described for formula I and formula II.

In another aspect, a compound that is useful in the process of producing the diazaspiro lactam compound of formula I is provided. The compound is a compound of formula III:

formula III

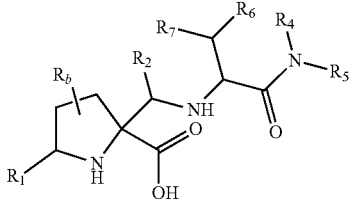

wherein $R_b$, $R_1$, $R_2$, $R_4$, $R_5$, $R_6$, and $R_7$ are the same as described for formula I and formula II.

In another aspect, another compound that is useful in the process of producing the diazaspiro lactam compound of formula I is provided. This compound is a compound of formula IV:

formula IV

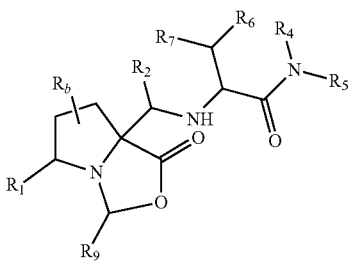

wherein $R_9$ is —CCl$_3$; and $R_b$, $R_1$, $R_2$, $R_4$, $R_5$, $R_6$, and $R_7$ are the same as described for formula I and formula II.

In another aspect, another compound that is useful in the process of producing the diazaspiro lactam compound of formula I is provided. This compound is a compound of formula V or VI:

formula V

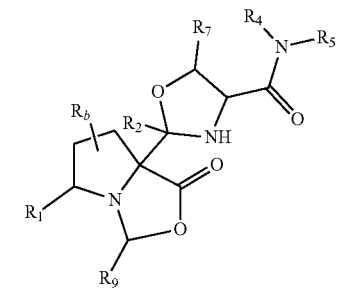

formula VI

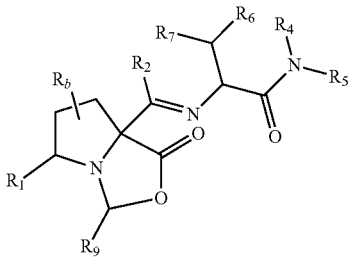

wherein $R_b$, $R_1$, $R_2$, $R_4$, $R_5$, and $R_7$ are the same as described for formula I and formula II, $R_9$ is the same as described for formula IV, and $R_6$ is selected from $C_1$-$C_6$ alkoxy, —OC(O)—$C_1$-$C_6$ alkyl, and —OC(O)phenyl.

In yet another aspect, a process of producing tert-butyl (S)-2-((2S,3R)-1-amino-3-hydroxy-1-oxobutan-2-yl)-1-oxo-2,5-diazaspiro[3.4]octane-5-carboxylate ("Compound A") is provided. This process comprises contacting Compound B and a coupling agent in an organic solvent to obtain Compound A:

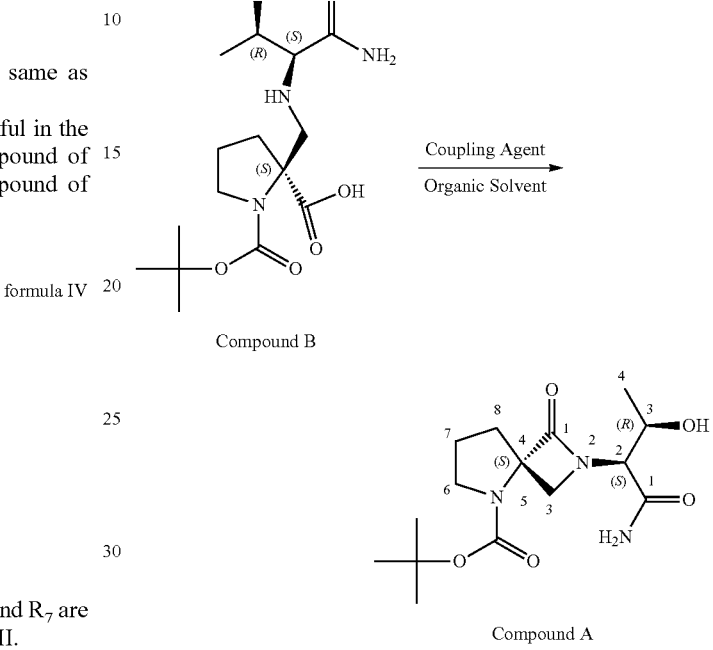

Compound B

Compound A

Some non-limiting example embodiments are listed below.

Example embodiment 1: A process of producing a compound of formula I or a pharmaceutically acceptable salt thereof, comprising contacting a compound of formula II with a coupling agent in an organic solvent to obtain a compound of formula I or a pharmaceutically acceptable salt thereof, wherein the coupling agent comprises an art recognized agent for coupling an amine and carboxylic acid to form an amide bond:

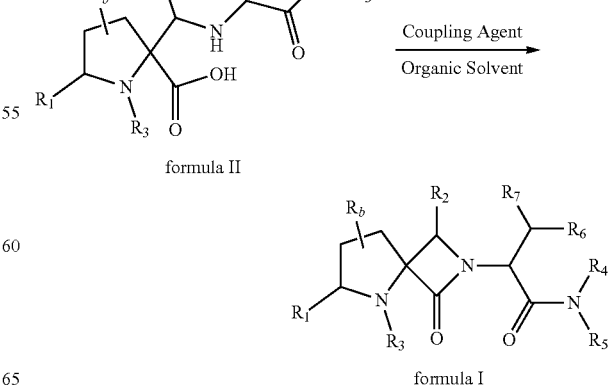

formula II formula I wherein:
R_b, is selected from H, halogen, cyano and $C_1$-$C_6$ alkyl;
$R_1$ is H or $C_1$-$C_6$ alkyl;
$R_2$ is H or $C_1$-$C_6$ alkyl;
$R_3$ is selected from $C_1$-$C_6$ alkyl and C(O)OR_8;
$R_8$ is selected from $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, and —CH_2—$C_3$-$C_{10}$ cycloalkyl, wherein $C_3$-$C_{10}$ cycloalkyl is optionally substituted with one, two, or three groups selected from $C_1$-$C_3$ alkyl;
$R_4$ and $R_5$ are independently selected from H, $C_1$-$C_6$ alkyl, X, and $C_1$-$C_6$ alkylene-X, wherein X is selected from:
  (i) $C_3$-$C_6$ cycloalkyl;
  (ii) heteroaryl including from 5 to 6 ring atoms wherein one, two, or three of the ring atoms are independently selected from N, NH, N($C_1$-$C_3$ alkyl), O, and S;
  (iii) heterocyclyl including from three to six ring atoms wherein 1, 2, or 3 of the ring atoms are independently selected from N, NH, N($C_1$-$C_3$alkyl), O, and S; and
  (iv) phenyl;
  wherein $C_3$-$C_6$ cycloalkyl, heterocyclyl, heteroaryl, and phenyl are each optionally substituted with one, two, or three substituents independently selected halogen, cyano, $C_1$-$C_6$ alkyl, hydroxyl, and $C_1$-$C_6$ alkoxy;
or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from N—$C_1$-$C_6$ alkyl, O and S; and wherein the heterocyclyl is optionally substituted with one, two, or three substituents independently selected from halogen, cyano, $C_1$-$C_6$ alkyl, and $C_1$-$C_6$ alkoxy;
$R_6$ is selected from —OH, $C_1$-$C_6$ alkoxy, —OC(O)—$C_1$-$C_6$ alkyl, and —OC(O)phenyl; and
$R_7$ is H or $C_1$-$C_6$ alkyl.

Example embodiment 2: The process of example embodiment 1, wherein the coupling agent comprises a carbodiimide optionally together with 1-hydroxybenzotriazole (HOBt).

Example embodiment 3: The process of example embodiment 2, wherein the coupling agent comprises a carbodiimide selected from dicyclohexylcarbodiimide (DCC), diisopropylcarbodiimide (DIC), and ethyl-(N',N'-dimethylamino)propylcarbodiimide hydrochloride (EDC).

Example embodiment 4: The process of example embodiment 1, wherein the coupling agent comprises at least one selected from (Benzotriazol-1-yloxy)tris(dimethylamino) phosphonium hexafluorophosphate (BOP), (Benzotriazol-1-yloxy)tripyrrolidinophosphonium hexafluorophosphate (PyBOP), (7-Azabenzotriazol-1-yloxy)tripyrrolidinophosphonium hexafluorophosphate (PyAOP), Bromotripyrrolidinophosphonium hexafluorophosphate (PyBrOP), Bis(2-oxo-3-oxazolidinyl)phosphinic chloride (BOP—Cl), O-(Benzotriazol-1-yl)-N,N,N',N'-tetramethyluronium hexafluorophosphate (HBTU), O-(Benzotriazol-1-yl)-N,N,N',N'-tetramethyluronium tetrafluoroborate (TBTU), O-(7-Azabenzotriazol-1-yl)-N,N,N',N'-tetramethyluronium hexafluorophosphate (HATU), O-(7-Azabenzotriazol-1-yl)-N,N,N',N'-tetramethyluronium tetrafluoroborate (TATU), O-(6-Chlorobenzotriazol-1-yl)-N,N,N',N'-tetramethyluronium hexafluorophosphate (HCTU), O-[(Ethoxycarbonyl)cyanomethylenamino]-N,N,N',N'-tetra methyluronium tetrafluoroborate (TOTU), (1-Cyano-2-ethoxy-2-oxoethylidenaminooxy)dimethylamino-morpholino-carbenium hexafluorophosphate (COMU), O—(N-Suc-cinimidyl)-1,1,3,3-tetramethyl-uronium tetrafluoroborate (TSTU), O-(5-Norbornene-2,3-dicarboximido)-N,N,N',N'-tetramethyluronium tetrafluoroborate (TNTU), O-(1,2-Dihydro-2-oxo-1-pyridyl-N,N,N',N'-tetramethyluronium tetrafluoroborate (TPTU), N,N,N',N'-Tetramethyl-O-(3,4-dihydro-4-oxo-1,2,3-benzotriazin-3-yl) uranium tetrafluoroborate (TDBTU), N,N,N',N'-Tetramethylchloroformamidinium Hexafluorophosphate (TCFH), 3-(Diethylphosphoryloxy)-1,2,3-benzotriazin-4 (3H)-one (DEPBT), and Carbonyldiimidazole (CDI).

Example embodiment 5: The process of example embodiment 1, wherein the coupling agent comprises a di-$C_1$-$C_6$ alkyl halophosphate, a dialkyl phosphinic halide, or propanephosphonic acid anhydride.

Example embodiment 6: The process of example embodiment 1, wherein the coupling agent comprises diethyl chlorophosphate.

Example embodiment 7: The process of any of example embodiments 1 to 6, wherein the coupling agent is used together with an organic base.

Example embodiment 8: The process of example embodiment 7, wherein the organic base comprises an amine.

Example embodiment 9: The process of example embodiment 8, wherein the organic base comprises triethyl amine, N,N-Diisopropylethylamine (DIPEA), or 4-Dimethylaminopyridine (DMAP).

Example embodiment 10: The process of any one of example embodiments 1 to 9, wherein the process is carried out in an organic solvent comprises dimethylformamide (DMF), dimethyl sulfoxide (DMSO), N-Methyl-2-pyrrolidone (NMP), acetonitrile (MeCN), dichloromethane (DCM), tetrahydrofuran (THF), or 2-methyltetrahydrofuran (2-MeTHF).

Example embodiment 11: The process of example embodiment 10, wherein the organic solvent comprises THF.

Example embodiment 12: The process of any one of example embodiments 1 to 11, further comprising contacting a compound of formula IV with a base in a solvent to obtain a compound of formula III, wherein the compound of formula III is subsequently contacted with an alkylating agent or carbamating agent to obtain a compound of formula II, wherein $R_b$, $R_1$, $R_2$, $R_3$, $R_4$, $R_5$, $R_6$, and $R_7$ are the same as described in example embodiment 1, and $R_9$ is —$CCl_3$:

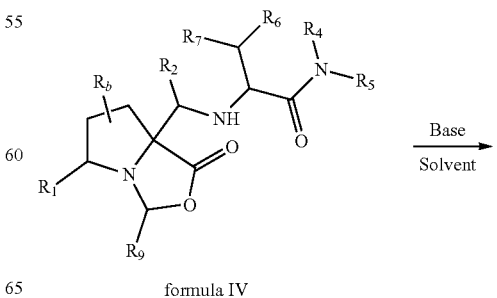

formula IV

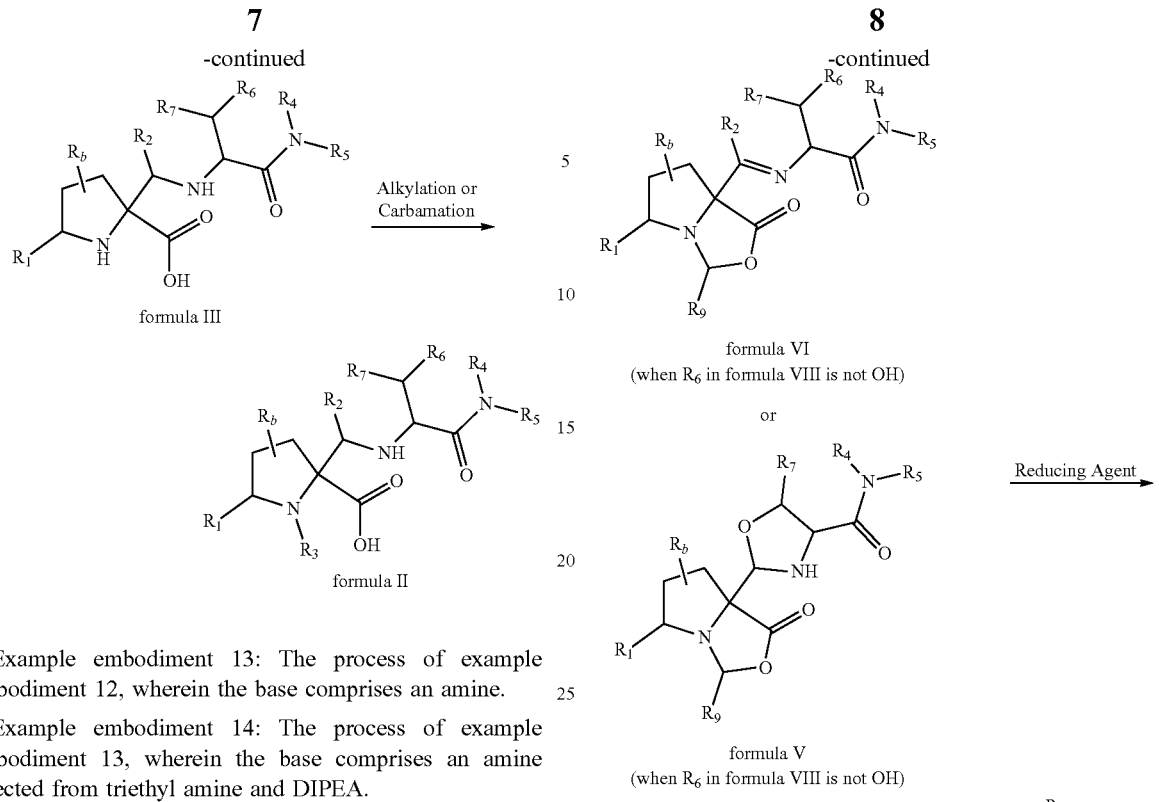

formula III formula II formula VI
(when R₆ in formula VIII is not OH)

or formula V
(when R₆ in formula VIII is not OH)

formula IV

Example embodiment 13: The process of example embodiment 12, wherein the base comprises an amine.

Example embodiment 14: The process of example embodiment 13, wherein the base comprises an amine selected from triethyl amine and DIPEA.

Example embodiment 15: The process of any one of example embodiments 12 to 14, wherein the solvent is an aqueous solvent.

Example embodiment 16: The process of any one of example embodiment 12 to 15, wherein the aqueous solvent comprises a mixture of water with acetonitrile, a mixture of water with THF, a mixture of water with 2-MeTHF, a mixture of water with methanol, a mixture of water with ethanol, a mixture of water with isopropanol, a mixture of water with DMF, or a mixture of water with DMSO.

Example embodiment 17: The process of any one of example embodiments 12 to 16, wherein the alkylating agent is $C_1$-$C_6$ alkyl-halide and the carbamating agent is di-$R_8$-dicarbonate, wherein $R_8$ is as defined in example embodiment 1.

Example embodiment 18: The process of any one of example embodiments 1 to 17, further comprising contacting a compound of formula VII with an amine of formula VIII to obtain a condensed product of formula V or VI, which is subsequently contacted with a reducing agent to obtain a compound of formula IV, wherein $R_b$, $R_1$, $R_2$, $R_3$, $R_4$, $R_5$, $R_6$, and $R_7$ are as defined in example embodiment 1, $R_9$ is as defined in example embodiment 12

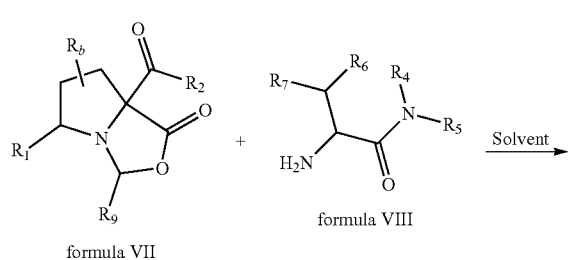

formula VII formula VIII

Example embodiment 19: The process of example embodiment 18, wherein the solvent for the condensation reaction comprises dichloromethane, dimethylformamide, tetrahydrofuran, or acetonitrile.

Example embodiment 20: The process of example embodiment 18, wherein the solvent for the condensation reaction comprises toluene.

Example embodiment 21: The process of any one of example embodiments 18 to 20, wherein, before contacting it with the reducing agent, the compound of formula V or VI is not isolated.

Example embodiment 22: The process of any one of example embodiments 18 to 21, wherein the reducing agent comprises a boron hydride.

Example embodiment 23: The process of example embodiment 22, wherein the reducing agent comprises a boron hydride selected from sodium borohydride, lithium borohydride, calcium borohydride, magnesium borohydride, sodium triacetoxyborohydride (NaBH(OAc)₃), NBu₄BH₄, NaCNBH₃, and NMe₄BH(OAc)₃.

Example embodiment 24: The process of example embodiment 23, wherein the reducing agent comprises sodium triacetoxyborohydride (NaBH(OAc)₃).

Example embodiment 25: The process of any one of example embodiments 1 to 24, further comprising contacting a compound of formula IX with a base known in the art to deprotonate the α carbon next to a carbonyl (CO) in a solvent, which is subsequently followed by addition of $R_2COOR$ to obtain the compound of formula VII, wherein R is methyl or ethyl, $R_b$, $R_1$, and $R_2$ are as defined in example embodiment 1 and $R_9$ is as defined in example embodiment 12:

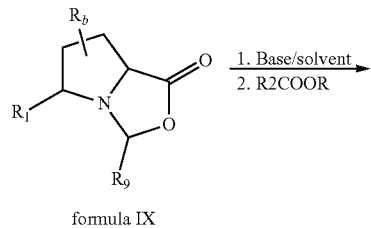

formula IX

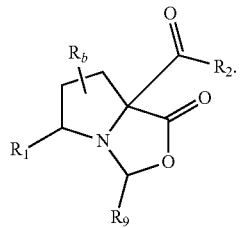

formula VII

Example embodiment 26: The process of example embodiment 25, wherein the deprotonation is conducted at a temperature below 0° C.

Example embodiment 27: The process of example embodiment 26, wherein the deprotonation is conducted at a temperature of −80 to −20° C.

Example embodiment 28: The process of any one of example embodiments 25 to 27, wherein the base comprises lithium diisopropylamide.

Example embodiment 29: The process of any one of example embodiments 25 to 28, wherein the solvent comprises toluene optionally mixed with methyl tert-butyl ether (MTBE), THF optionally mixed with toluene or MTBE, or 2-MeTHF optionally mixed with toluene or MTBE.

Example embodiment 30: The process of any one of example embodiments 25 to 29, wherein $R_2C(O)OR$ is added to the deprotonated formula IX at a temperature below 0° C.

Example embodiment 31: The process of example embodiment 30, wherein $R_2C(O)OR$ is added to the deprotonated formula IX at a temperature of −80 to −20° C.

Example embodiment 32: The process of example embodiment 31, wherein $R_2C(O)OR$ is added to the deprotonated formula IX at a temperature of about −60° C.

Example embodiment 33: The process of any one of example embodiments 1 to 32, further comprising contacting a compound of formula X with an aldehyde $R_9CHO$, or hydrate thereof, to obtain a compound of formula IX, wherein $R_b$ and $R_1$ are as defined in example embodiment 1 and $R_9$ is as defined in example embodiment 12:

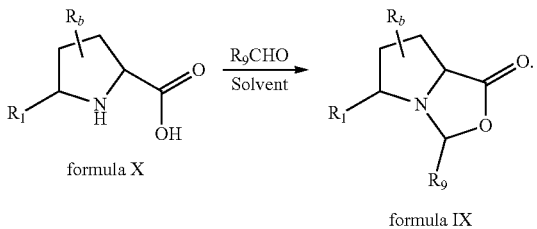

Example embodiment 34: The process of example embodiment 33, wherein the solvent used to obtain the compound of formula IX comprises THF, acetonitrile, or toluene.

Example embodiment 35: The process of any one of example embodiments 1 to 34, wherein:
$R_b$ is selected from H, halogen, cyano and $C_1$-$C_6$ alkyl;
$R_1$ is H or $C_1$-$C_6$ alkyl;
$R_2$ is H or $C_1$-$C_6$ alkyl;
$R_3$ is selected from $C_1$-$C_6$ alkyl and $C(O)OR_8$;
$R_8$ is selected from $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, and —$CH_2$—$C_3$-$C_{10}$ cycloalkyl, wherein $C_3$-$C_{10}$ cycloalkyl is optionally substituted with one, two, or three groups selected from $C_1$-$C_3$ alkyl;
$R_4$ and $R_5$ are independently selected from H and $C_1$-$C_6$ alkyl; or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from N—$C_1$-$C_6$ alkyl, O and S; and wherein the heterocyclyl is optionally substituted with one, two, or three substituents independently selected from halogen, cyano, $C_1$-$C_6$ alkyl, and $C_1$-$C_6$ alkoxy;
$R_6$ is selected from —OH, $C_1$-$C_6$ alkoxy, —OC(O)—$C_1$-$C_6$ alkyl, and —OC(O)phenyl;
$R_7$ is H or $C_1$-$C_6$ alkyl; and
$R_9$ is selected from $CCl_3$.

Example embodiment 36: The process of example embodiment 35, wherein $R_1$ and $R_2$ are H.

Example embodiment 37: The process of example embodiment 35, wherein each of $R_1$, $R_2$, $R_4$, and $R_5$ is H.

Example embodiment 38: The process of any one of example embodiments 35 to 37, wherein $R_6$ is OH.

Example embodiment 39: The process of any one of example embodiments 35 to 38, wherein $R_7$ is $C_1$-$C_6$ alkyl.

Example embodiment 40: The process of example embodiment 39, wherein $R_7$ is methyl.

Example embodiment 41: The process of any one of example embodiments 35 to 40, wherein $R_3$ is $OC(O)R_8$.

Example embodiment 42: The process of example embodiment 41, wherein $R_8$ is $C_1$-$C_6$ alkyl.

Example embodiment 43: The process of example embodiment 42, wherein $R_8$ is tertiary butyl.

Example embodiment 44: A process of producing tert-butyl (S)-2-((2S,3R)-1-amino-3-hydroxy-1-oxobutan-2-yl)-1-oxo-2,5-diazaspiro[3.4]octane-5-carboxylate ("Compound A"), comprising contacting Compound B and a coupling agent in an organic solvent to obtain Compound A, wherein the coupling agent comprises an art recognized agent for coupling an amine and carboxylic acid to form an amide bond:

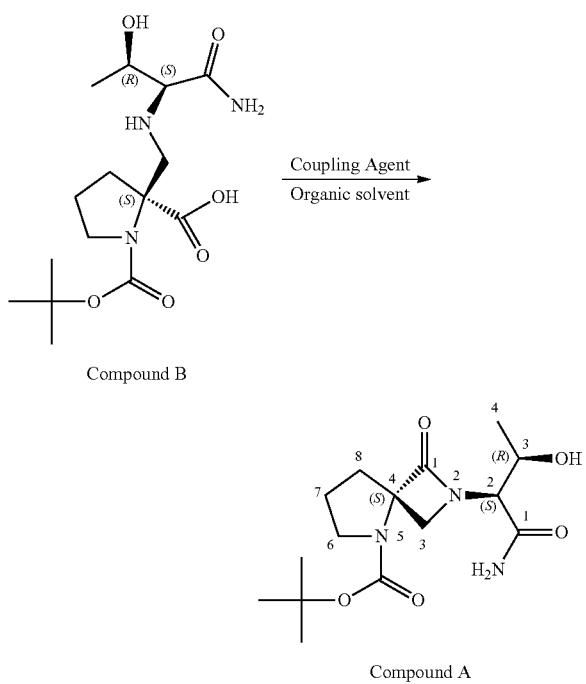

Compound B

Compound A and wherein Compound B is obtained by contacting Compound C with di-tert-butyl dicarbonate (BOC₂O) in an organic solvent:

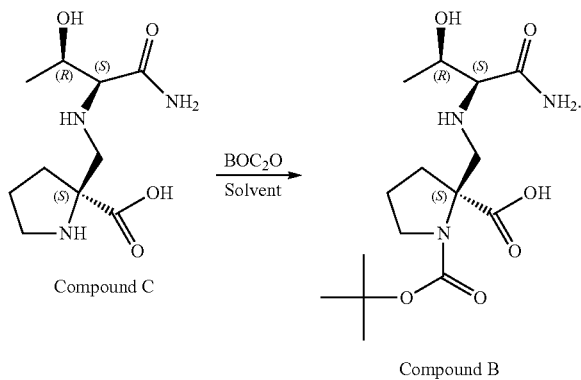

Compound C

Compound B

Example embodiment 45: The process of example embodiment 44, wherein the coupling agent comprises a carbodiimide optionally together with 1-hydroxybenzotriazole (HOBt).

Example embodiment 46: The process of example embodiment 45, wherein the coupling agent comprises a carbodiimide selected from dicyclohexylcarbodiimide (DCC), diisopropylcarbodiimide (DIC), and ethyl-(N',N'-dimethylamino)propylcarbodiimide hydrochloride (EDC).

Example embodiment 47: The process of example embodiment 44, wherein the coupling agent comprises (Benzotriazol-1-yloxy)tris(dimethylamino)phosphonium hexafluorophosphate (BOP), (Benzotriazol-1-yloxy)tripyrrolidinophosphonium hexafluorophosphate (PyBOP), (7-Azabenzotriazol-1-yloxy)tripyrrolidinophosphonium hexafluorophosphate (PyAOP), Bromotripyrrolidinophosphonium hexafluorophosphate (PyBrOP), Bis(2-oxo-3-oxazolidinyl)phosphinic chloride (BOP—Cl), O-(Benzotriazol-1-yl)-N,N,N',N'-tetramethyluronium hexafluorophosphate (HBTU), O-(Benzotriazol-1-yl)-N,N,N',N'-tetramethyluronium tetrafluoroborate (TBTU), O-(7-Azabenzotriazol-1-yl)-N,N,N',N'-tetramethyluronium hexafluorophosphate (HATU), O-(7-Azabenzotriazol-1-yl)-N,N,N',N'-tetramethyluronium tetrafluoroborate (TATU), O-(6-Chlorobenzotriazol-1-yl)-N,N,N',N'-tetramethyluronium hexafluorophosphate (HCTU), O-[(Ethoxycarbonyl)cyanomethylenamino]-N,N,N',N'-tetra methyluronium tetrafluoroborate (TOTU), (1-Cyano-2-ethoxy-2-oxoethylidenaminooxy)dimethylamino-morpholino-carbenium hexafluorophosphate (COMU), O—(N-Suc-cinimidyl)-1,1,3,3-tetramethyl-uronium tetrafluoroborate (TSTU), O-(5-Norbornene-2,3-dicarboximido)-N,N,N',N'-tetramethyluronium tetrafluoroborate (TNTU), O-(1,2-Dihydro-2-oxo-1-pyridyl-N,N,N',N'-tetramethyluronium tetrafluoroborate (TPTU), N,N,N',N'-Tetramethyl-O-(3,4-dihydro-4-oxo-1,2,3-benzotriazin-3-yl)uranium tetrafluoroborate (TDBTU), N,N,N',N'-Tetramethylchloroformamidinium Hexafluorophosphate (TCFH), 3-(Diethylphosphoryloxy)-1,2,3-benzotriazin-4(3H)-one (DEPBT), or Carbonyldiimidazole (CDI).

Example embodiment 48: The process of example embodiment 44, wherein the coupling agent comprises a di-$C_1$-$C_6$ alkyl halophosphate, a dialkyl phosphinic halide, or propanephosphonic acid anhydride.

Example embodiment 49: The process of example embodiment 48, wherein the coupling agent comprises diethyl chlorophosphate.

Example embodiment 50: The process of any one of example embodiments 44 to 49, wherein the coupling agent is used together with an organic base.

Example embodiment 51: The process of example embodiment 50, wherein the organic base comprises an amine.

Example embodiment 52: The process of example embodiment 51, wherein the organic base comprises triethyl amine, N,N-Diisopropylethylamine (DIPEA), or 4-Dimethylaminopyridine (DMAP).

Example embodiment 53: The process of example embodiment 52, wherein the organic base comprises triethyl amine.

Example embodiment 54: The process of any one of example embodiments 44 to 53, wherein the organic solvent used to prepare Compound A comprises dimethylformamide (DMF), dimethyl sulfoxide (DMSO), N-Methyl-2-pyrrolidone (NMP), acetonitrile (MeCN), dichloromethane (DCM), tetrahydrofuran (THF), or 2-methyltetrahydrofuran (2-MeTHF).

Example embodiment 55: The process of example embodiment 54, wherein the solvent comprises THF.

Example embodiment 56: The process of any one of example embodiments 44 to 55, wherein the solvent used to prepare Compound B comprises acetonitrile, methanol, ethanol, isopropanol, MTBE, toluene, acetone, $CH_2Cl_2$, THF, 2-MeTHF, water, and mixtures thereof.

Example embodiment 57: The process of any one of example embodiments 44 to 56, further comprising contacting Compound D with a base in a solvent to obtain Compound C:

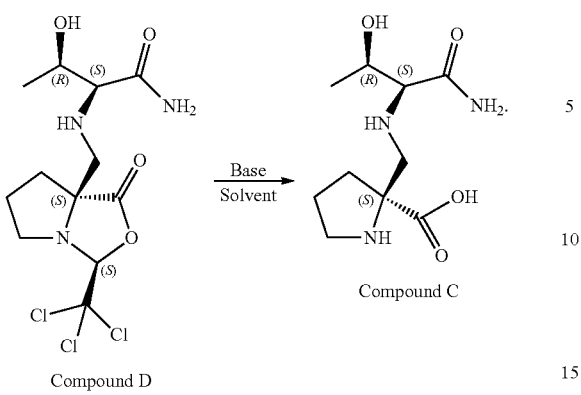

Compound D → Compound C

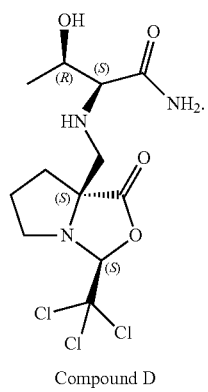

Compound D

Example embodiment 58: The process of example embodiment 57, wherein the base comprises an amine.

Example embodiment 59: The process of example embodiment 58, wherein the base comprises triethyl amine or DIPEA.

Example embodiment 60: The process of any one of example embodiments 56 to 59, wherein the solvent is an aqueous solvent.

Example embodiment 61: The process of example embodiment 60, wherein the aqueous solvent comprises a mixture of water with acetonitrile, a mixture of water with THF, a mixture of water with 2-MeTHF, a mixture of water with methanol, a mixture of water with ethanol, a mixture of water with isopropanol, a mixture of water with DMF, or a mixture of water with DMSO.

Example embodiment 62: The process of any one of example embodiments 44 to 61, further comprising condensing Compound F with Compound G to obtain Compound E which is subsequently contacted with a reducing agent to obtain Compound D:

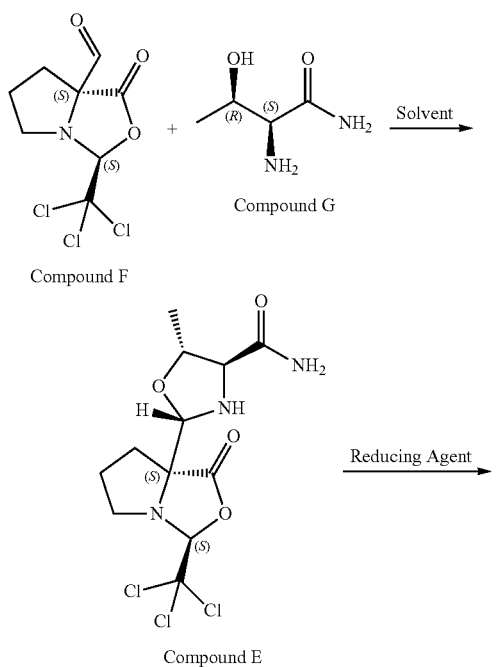

Example embodiment 63: The process of example embodiment 62, wherein the solvent for the condensation reaction comprises dichloromethane.

Example embodiment 64: The process of example embodiment 62, wherein the solvent for the condensation reaction comprises toluene.

Example embodiment 65: The process of any one of example embodiments 62 to 64, wherein the reducing agent comprises a boron hydride.

Example embodiment 66: The process of any of example embodiment 65, wherein the reducing agent comprises a boron hydride selected from sodium borohydride, lithium borohydride, calcium borohydride, magnesium borohydride, sodium triacetoxyborohydride (NaBH(OAc)$_3$), NBu$_4$BH$_4$, NaCNBH$_3$, and NMe$_4$BH(OAc)$_3$.

Example embodiment 67: The process of any one of example embodiments 62 to 66, wherein, before contacting it with the reducing agent, Compound E is not isolated.

Example embodiment 68: The process of any one of example embodiments 44 to 67, further comprising contacting Compound H with a base known in the art to deprotonate the α carbon next to a carbonyl (CO) in a solvent, which is subsequently followed by contact with HCOOR, wherein R is methyl or ethyl, to obtain Compound F:

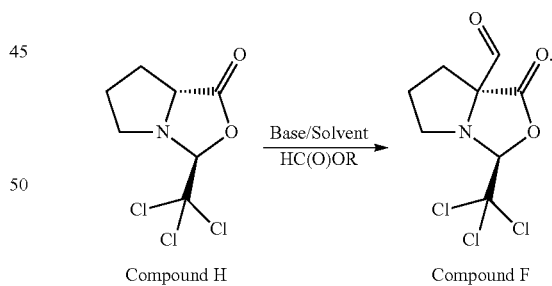

Example embodiment 69: The process of example embodiment 68, wherein the deprotonation is conducted at a temperature below 0° C.

Example embodiment 70: The process of example embodiment 69, wherein the deprotonation is conducted at a temperature of −80 to −20° C.

Example embodiment 71: The process of example embodiment 70, wherein the deprotonation is conducted at a temperature of about −45° C.

Example embodiment 72: The process of any one of example embodiments 68 to 71, wherein the base comprises lithium diisopropylamide.

Example embodiment 73: The process of any one of example embodiments 68 to 72, wherein the solvent comprises methyl tert-butyl ether (MTBE), toluene optionally mixed with MTBE, THF optionally mixed with toluene, THF optionally mixed with MTBE, 2-MeTHF optionally mixed with toluene, or 2-MeTHF optionally mixed with MTBE.

Example embodiment 74: The process of any one of example embodiments 68 to 73, wherein HC(O)OR is added to the deprotonated Compound H at a temperature below 0° C.

Example embodiment 75: The process of example embodiment 74, wherein HC(O)OR is added to the deprotonated Compound H at a temperature of −80 to −20° C.

Example embodiment 76: The process of example embodiment 75, wherein HC(O)OR is added to the deprotonated Compound H at a temperature of about −60° C.

Example embodiment 77: The process of any one of example embodiments 44 to 76, further comprising contacting D-proline with chloral to obtain Compound H:

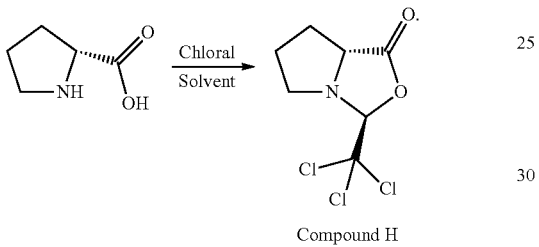

Compound H

Example embodiment 78: The process of example embodiment 77, wherein the solvent used to obtain Compound H comprises THF, 2-MeTHF, acetonitrile, toluene, dichloromethane, chloroform, or MTBE.

Example embodiment 79: The process of example embodiment 78, wherein the solvent used to obtain Compound H comprises acetonitrile.

Example embodiment 80: A compound of formula II:

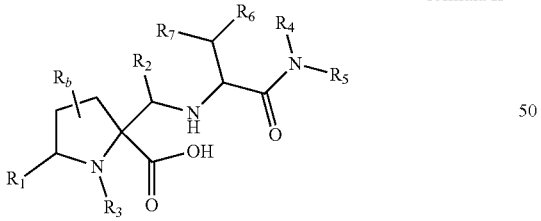

formula II wherein:

$R_b$ is selected from H, halogen, cyano and $C_1$-$C_6$ alkyl;

$R_1$ is H or $C_1$-$C_6$ alkyl;

$R_2$ is H or $C_1$-$C_6$ alkyl;

$R_3$ is selected from $C_1$-$C_6$ alkyl and C(O)O$R_8$;

$R_8$ is selected from $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, and —$CH_2$—$C_3$-$C_{10}$ cycloalkyl, wherein $C_3$-$C_{10}$ cycloalkyl is optionally substituted with one, two, or three groups selected from $C_1$-$C_3$ alkyl;

$R_4$ and $R_5$ are independently selected from H, $C_1$-$C_6$ alkyl, X, and —$C_1$-$C_6$ alkylene-X, wherein X is selected from (i) $C_3$-$C_6$ cycloalkyl;

(ii) heteroaryl including from 5 to 6 ring atoms wherein one, two, or three of the ring atoms are independently selected from N, NH, N($C_1$-$C_3$ alkyl), O, and S;

(iii) heterocyclyl including from three to six ring atoms wherein 1, 2, or 3 of the ring atoms are independently selected from N, NH, N($C_1$-$C_3$ alkyl), O, and S; and (iv) phenyl;

wherein $C_3$-$C_6$ cycloalkyl, heterocyclyl, heteroaryl, and phenyl are each optionally substituted with one, two, or three substituents independently selected halogen, cyano, $C_1$-$C_6$ alkyl, hydroxyl, and $C_1$-$C_6$ alkoxy;

or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from N—$C_1$-$C_6$ alkyl, O and S; and wherein the heterocyclyl is optionally substituted with one, two, or three substituents independently selected from halogen, cyano, $C_1$-$C_6$ alkyl, and $C_1$-$C_6$ alkoxy;

$R_6$ is selected from —OH, $C_1$-$C_6$ alkoxy, —OC(O)—$C_1$-$C_6$ alkyl, and —OC(O)phenyl; and $R_7$ is H or $C_1$-$C_6$ alkyl.

Example embodiment 81: The compound of example embodiment 80, wherein the compound of formula II is a compound of formula IIa:

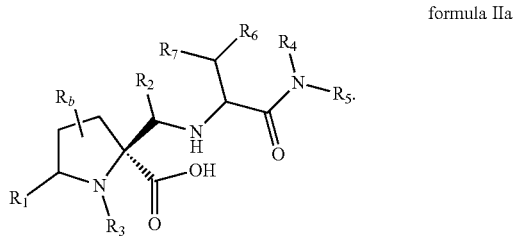

formula IIa

Example embodiment 82: The compound of example embodiment 81, wherein the compound of formula IIa is a compound of formula IIb:

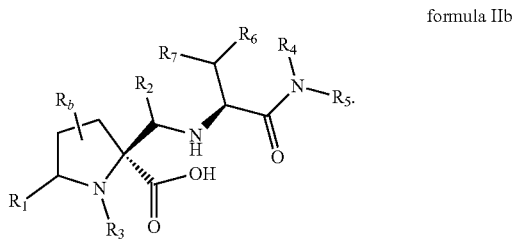

formula IIb

Example embodiment 83: The compound of example embodiment 82, wherein the compound of formula IIb is a compound of formula IIc:

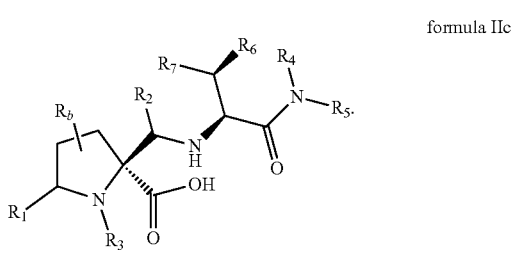

formula IIc

Example embodiment 84: The compound of any one of example embodiments 80 to 83, wherein:

$R_b$ is selected from H, halogen, cyano and $C_1$-$C_6$ alkyl;

$R_1$ is H or $C_1$-$C_6$ alkyl;

$R_2$ is H or $C_1$-$C_6$ alkyl;

$R_3$ is selected from $C_1$-$C_6$ alkyl and C(O)O$R_8$;

$R_8$ is selected from $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, and —$CH_2$—$C_3$-$C_{10}$ cycloalkyl, wherein $C_3$-$C_{10}$ cycloalkyl is optionally substituted with one, two, or three groups selected from $C_1$-$C_3$ alkyl;

$R_4$ and $R_5$ are independently selected from H and $C_1$-$C_6$ alkyl; or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from N—$C_1$-$C_6$ alkyl, O and S; and wherein the heterocyclyl is optionally substituted with one, two, or three substituents independently selected from halogen, cyano, $C_1$-$C_6$ alkyl, and $C_1$-$C_6$ alkoxy;

$R_6$ is selected from —OH, $C_1$-$C_6$ alkoxy, —OC(O)—$C_1$-$C_6$ alkyl, and —OC(O)phenyl; and $R_7$ is H or $C_1$-$C_6$ alkyl.

Example embodiment 85: The compound of example embodiment 84, wherein $R_1$ and $R_2$ are H.

Example embodiment 86: The compound of example embodiment 84, wherein each of $R_1$, $R_2$, $R_4$, and $R_5$ is H.

Example embodiment 87: The compound of any one of example embodiments 84 to 86, wherein $R_6$ is OH.

Example embodiment 88: The compound of any one of example embodiments 84 to 87, wherein $R_7$ is $C_1$-$C_6$ alkyl.

Example embodiment 89: The compound of example embodiment 88, wherein $R_7$ is methyl.

Example embodiment 90: The compound of any one of example embodiments 84 to 89, wherein $R_3$ is OC(O)$R_8$, $R_8$ is $C_1$-$C_6$ alkyl.

Example embodiment 91: The compound of example embodiment 90, wherein $R_8$ is tertiary butyl.

Example embodiment 92: The compound of example embodiment 80, wherein the compound of formula II is selected from the following compounds:

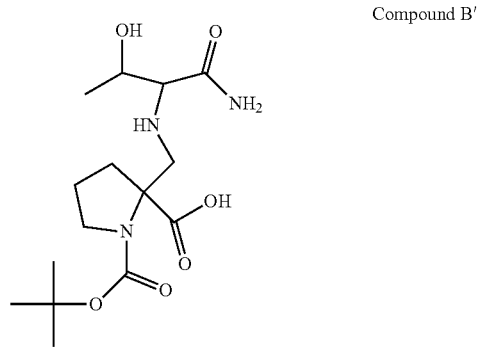

Compound B'

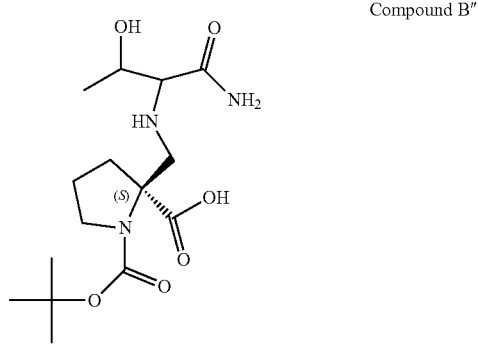

Compound B''

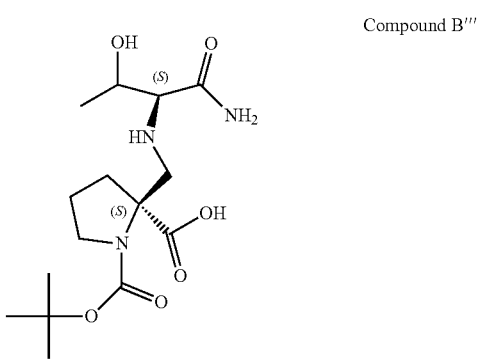

Compound B'''

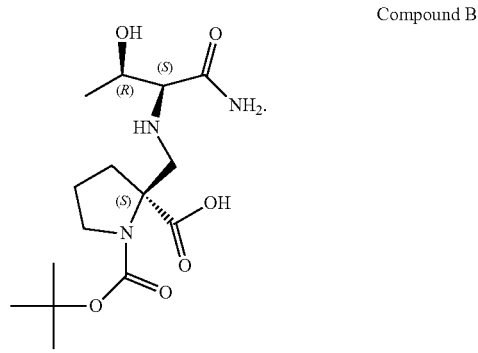

Compound B

Example embodiment 93: The compound of example embodiment 92, wherein the compound of formula II is Compound B.

Example embodiment 94: A compound of formula III:

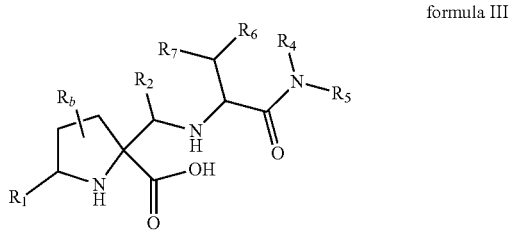

formula III wherein:
R$_b$ is selected from H, halogen, cyano and C$_1$-C$_6$ alkyl;
R$_1$ is H or C$_1$-C$_6$ alkyl;
R$_2$ is H or C$_1$-C$_6$ alkyl;
R$_8$ is selected from C$_1$-C$_6$ alkyl, C$_1$-C$_6$ haloalkyl, C$_2$-C$_6$ alkenyl, C$_2$-C$_6$ alkynyl, C$_3$-C$_{10}$ cycloalkyl, and —CH$_2$—C$_3$-C$_{10}$ cycloalkyl, wherein C$_3$-C$_{10}$ cycloalkyl is optionally substituted with one, two, or three groups selected from C$_1$-C$_3$ alkyl;
R$_4$ and R$_5$ are independently selected from H, C$_1$-C$_6$ alkyl, X, and —C$_1$-C$_6$ alkylene-X, wherein X is selected from
  (i) C$_3$-C$_6$ cycloalkyl;
  (ii) heteroaryl including from 5 to 6 ring atoms wherein one, two, or three of the ring atoms are independently selected from N, NH, N(C$_1$-C$_3$ alkyl), O, and S;
  (iii) heterocyclyl including from three to six ring atoms wherein 1, 2, or 3 of the ring atoms are independently selected from N, NH, N(C$_1$-C$_3$ alkyl), O, and S; and
  (iv) phenyl;
  wherein C$_3$-C$_6$ cycloalkyl, heterocyclyl, heteroaryl, and phenyl are each optionally substituted with one, two, or three substituents independently selected halogen, cyano, C$_1$-C$_6$ alkyl, hydroxyl, and C$_1$-C$_6$alkoxy;
or R$_4$ and R$_5$ together with the nitrogen to which they are attached form heterocyclyl including from 4 to 6 ring atoms; wherein the heterocyclyl includes not more than two ring heteroatoms (including the nitrogen atom attached to R$_4$ and R$_5$), and the second ring heteroatom, when present, is independently selected from N—C$_1$-C$_6$ alkyl, O and S; and wherein the heterocyclyl is optionally substituted with one, two, or three substituents independently selected from halogen, cyano, C$_1$-C$_6$alkyl, and C$_1$-C$_6$ alkoxy;
R$_6$ is selected from —OH, C$_1$-C$_6$ alkoxy, —OC(O)—C$_1$-C$_6$ alkyl, and —OC(O)phenyl; and
R$_7$ is H or C$_1$-C$_6$ alkyl.

Example embodiment 95: The compound of example embodiment 94, wherein the compound of formula III is a compound of formula IIIa:

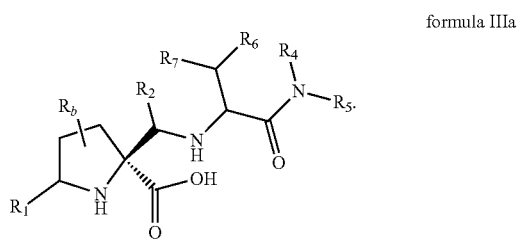

formula IIIa

Example embodiment 96: The compound of example embodiment 95, wherein the compound of formula IIIa is a compound of formula IIIb:

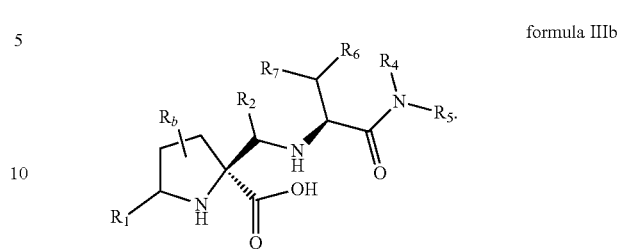

formula IIIb

Example embodiment 97: The compound of example embodiment 96, wherein the compound of formula IIIb is a compound of formula IIIc:

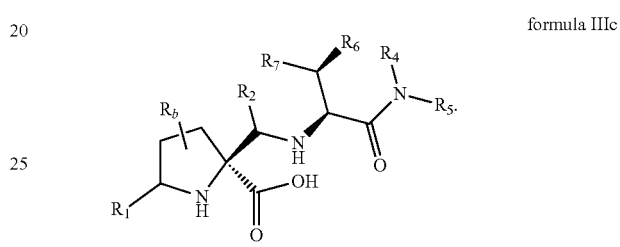

formula IIIc

Example embodiment 98: The compound of any one of example embodiments 94 to 97, wherein:
R$_b$ is selected from H, halogen, cyano and C$_1$-C$_6$ alkyl;
R$_1$ is H or C$_1$-C$_6$ alkyl;
R$_2$ is H or C$_1$-C$_6$ alkyl;
R$_8$ is selected from C$_1$-C$_6$ alkyl, C$_1$-C$_6$ haloalkyl, C$_2$-C$_6$ alkenyl, C$_2$-C$_6$ alkynyl, C$_3$-C$_{10}$ cycloalkyl, and —CH$_2$—C$_3$-C$_{10}$ cycloalkyl, wherein C$_3$-C$_{10}$ cycloalkyl is optionally substituted with one, two, or three groups selected from C$_1$-C$_3$ alkyl;
R$_4$ and R$_5$ are independently selected from H and C$_1$-C$_6$ alkyl; or R$_4$ and R$_5$ together with the nitrogen to which they are attached form heterocyclyl including from 4 to 6 ring atoms; wherein the heterocyclyl includes not more than two ring heteroatoms (including the nitrogen atom attached to R$_4$ and R$_5$), and the second ring heteroatom, when present, is independently selected from N—C$_1$-C$_6$ alkyl, O and S; and wherein the heterocyclyl is optionally substituted with one, two, or three substituents independently selected from halogen, cyano, C$_1$-C$_6$ alkyl, and C$_1$-C$_6$ alkoxy;
R$_6$ is selected from —OH, C$_1$-C$_6$ alkoxy, —OC(O)—C$_1$-C$_6$ alkyl, and —OC(O)phenyl; and
R$_7$ is H or C$_1$-C$_6$ alkyl.

Example embodiment 99: The compound of example embodiment 98, wherein R$_1$ and R$_2$ are H.

Example embodiment 100: The compound of example embodiment 98, wherein each of R$_1$, R$_2$, R$_4$, and R$_5$ is H.

Example embodiment 101: The compound of any one of example embodiments 98 to 100, wherein R$_6$ is OH.

Example embodiment 102: The compound of any one of example embodiments 98 to 101, wherein R$_7$ is C$_1$-C$_6$ alkyl.

Example embodiment 103: The compound of example embodiment 102, wherein R$_7$ is methyl.

Example embodiment 104: The compound of any one of example embodiments 98 to 103, wherein R$_3$ is OC(O)R$_8$, R$_8$ is C$_1$-C$_6$ alkyl.

Example embodiment 105: The compound of example embodiment 104, wherein R$_8$ is tertiary butyl.

Example embodiment 106: The compound of example embodiment 94, wherein the compound of formulae III is selected from the following compounds:

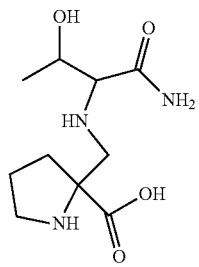
Compound C'

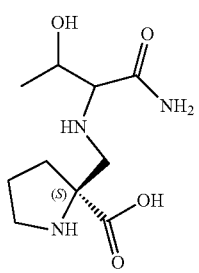
Compound C''

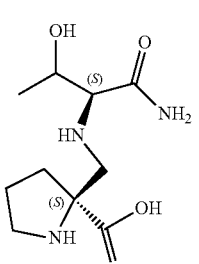
Compound C'''

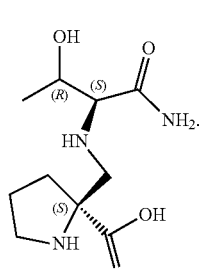
Compound C

Example embodiment 107: The compound of example embodiment 106, wherein the compound of formula II is Compound C.

Example embodiment 108: A compound of formula IV:

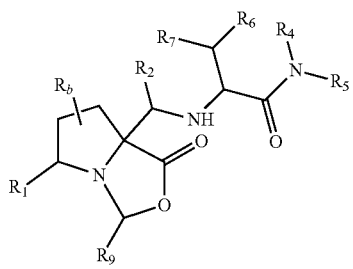
formula IV wherein:
$R_b$ is selected from H, halogen, cyano and $C_1$-$C_6$ alkyl;
$R_1$ is H or $C_1$-$C_6$ alkyl,
$R_2$ is H or $C_1$-$C_6$ alkyl;
$R_4$ and $R_5$ are independently selected from H, $C_1$-$C_6$ alkyl, X, and —$C_1$-$C_6$ alkylene-X, wherein X is selected from:
(i) $C_3$-$C_6$ cycloalkyl;
(ii) heteroaryl including from 5 to 6 ring atoms wherein one, two, or three of the ring atoms are independently selected from N, NH, N($C_1$-$C_3$ alkyl), O, and S;
(iii) heterocyclyl including from three to six ring atoms wherein 1, 2, or 3 of the ring atoms are independently selected from N, NH, N($C_1$-$C_3$ alkyl), O, and S; and
(iv) phenyl;
wherein $C_3$-$C_6$ cycloalkyl, heterocyclyl, heteroaryl, and phenyl are each optionally substituted with one, two, or three substituents independently selected halogen, cyano, $C_1$-$C_6$ alkyl, hydroxyl, and $C_1$-$C_6$ alkoxy;
or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from N—$C_1$-$C_6$ alkyl, O and S; and wherein the heterocyclyl is optionally substituted with one, two, or three substituents independently selected from halogen, cyano, $C_1$-$C_6$ alkyl, and $C_1$-$C_6$ alkoxy;
$R_6$ is selected from —OH, $C_1$-$C_6$ alkoxy, —OC(O)—$C_1$-$C_6$ alkyl, and —OC(O)phenyl; and
$R_7$ is H or $C_1$-$C_6$ alkyl; and
$R_9$ is —$CCl_3$.

Example embodiment 109: The compound of example embodiment 108, wherein the compound of formula IV is a compound of formula IVa:

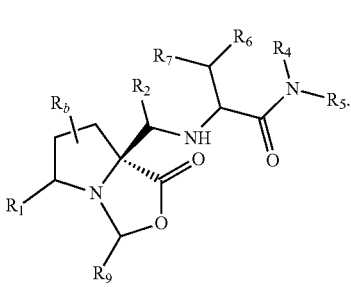
formula IVa

Example embodiment 110: The compound of example embodiment 109, wherein the compound of formula IVa is a compound of formula IVb:

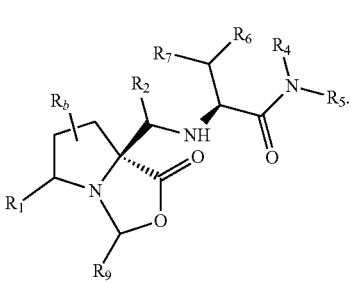
formula IVb

Example embodiment 111: The compound of example embodiment 110, wherein the compound of formula IVb is a compound of formula IVc:

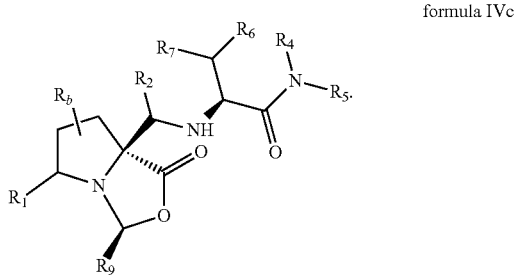

formula IVc

Example embodiment 112: The compound of example embodiment 111, wherein the compound of formula IVc is a compound of formula IVd:

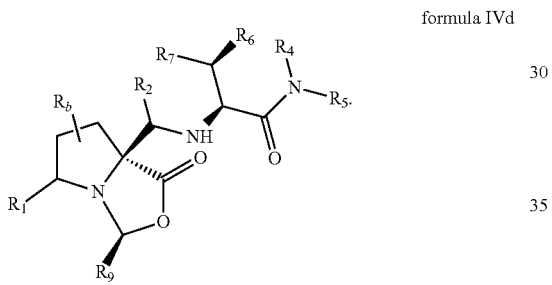

formula IVd

Example embodiment 113: The compound of any one of example embodiments 108 to 112, wherein
$R_b$ is selected from H, halogen, cyano and $C_1$-$C_6$ alkyl;
$R_1$ is H or $C_1$-$C_6$ alkyl;
$R_2$ is H or $C_1$-$C_6$ alkyl;
$R_4$ and $R_5$ are independently selected from H and $C_1$-$C_6$ alkyl; or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from N—$C_1$-$C_6$ alkyl, O and S; and wherein the heterocyclyl is optionally substituted with one, two, or three substituents independently selected from halogen, cyano, $C_1$-$C_6$ alkyl, and $C_1$-$C_6$alkoxy;
$R_6$ is selected from —OH, $C_1$-$C_6$ alkoxy, —OC(O)—$C_1$-$C_6$ alkyl, and —OC(O)phenyl;
$R_7$ is H or $C_1$-$C_6$ alkyl; and
$R_9$ is —CCl$_3$.

Example embodiment 114: The compound of example embodiment 113, wherein $R_1$ and $R_2$ are H.

Example embodiment 115: The compound of example embodiment 113 or 114, wherein $R_9$ is CCl$_3$.

Example embodiment 116: The compound of any one of example embodiments 113 to 115, wherein each of $R_1$, $R_2$, $R_4$, and $R_5$ is H.

Example embodiment 117: The compound of any one of example embodiments 113 to 116, wherein $R_6$ is OH.

Example embodiment 118: The compound of any one of example embodiments 113 to 117, wherein $R_7$ is $C_1$-$C_6$ alkyl.

Example embodiment 119: The compound of example embodiment 118, wherein $R_7$ is methyl.

Example embodiment 120: The compound of example embodiment 108, wherein the compound of formula IV is selected from the following compounds:

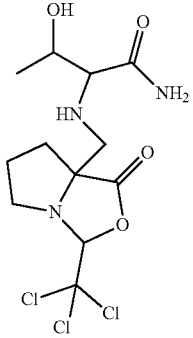

Compound D'

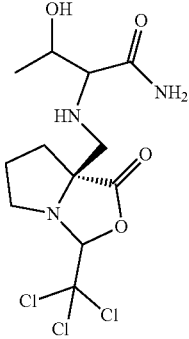

Compound D''

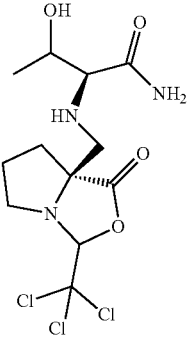

Compound D'''

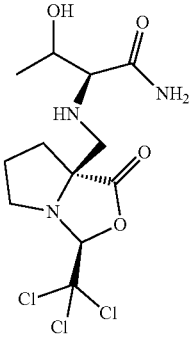

Compound D''''

-continued

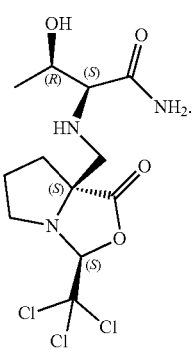

Compound D

Example embodiment 121: The compound of example embodiment 120, wherein the compound of formula IV is compound D.

Example embodiment 122: A compound of formula V or VI:

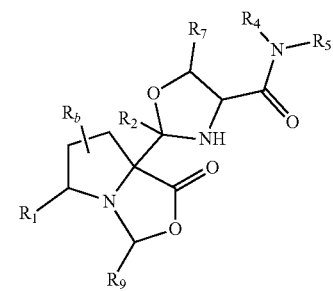

formula V

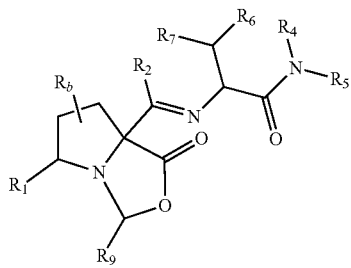

formula VI wherein:
$R_b$ is selected from H, halogen, cyano and $C_1$-$C_6$ alkyl;
$R_1$ is H or $C_1$-$C_6$ alkyl;
$R_2$ is H or $C_1$-$C_6$ alkyl;
$R_4$ and $R_5$ are independently selected from H, $C_1$-$C_6$ alkyl, X, and —$C_1$-$C_6$ alkylene-X, wherein X is selected from:
  (i) $C_3$-$C_6$ cycloalkyl;
  (ii) heteroaryl including from 5 to 6 ring atoms wherein one, two, or three of the ring atoms are independently selected from N, NH, N($C_1$-$C_3$ alkyl), O, and S;
  (iii) heterocyclyl including from three to six ring atoms wherein 1, 2, or 3 of the ring atoms are independently selected from N, NH, N($C_1$-$C_3$ alkyl), O, and S; and
  (iv) phenyl;
wherein $C_3$-$C_6$ cycloalkyl, heterocyclyl, heteroaryl, and phenyl are each optionally substituted with one, two, or three substituents independently selected halogen, cyano, $C_1$-$C_6$ alkyl, hydroxyl, and $C_1$-$C_6$ alkoxy;

or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from N—$C_1$-$C_6$ alkyl, O and S; and wherein the heterocyclyl is optionally substituted with one, two, or three substituents independently selected from halogen, cyano, $C_1$-$C_6$ alkyl, and $C_1$-$C_6$ alkoxy;
$R_6$ is selected from $C_1$-$C_6$ alkoxy, —OC(O)—$C_1$-$C_6$ alkyl, and —OC(O)phenyl;
$R_7$ is H or $C_1$-$C_6$ alkyl; and Example embodiment 123: The compound of example embodiment 122, wherein the compound of formula V and the compound of formula VI are a compound of formula Va and a compound of formula VIa, respectively:

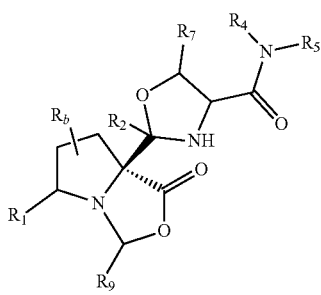

formula Va

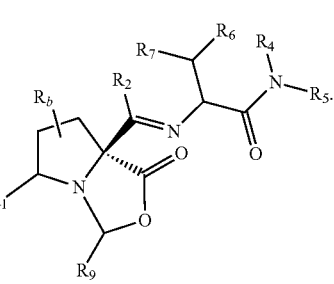

formula VIa

Example embodiment 124: The compound of example embodiment 123, wherein the compound of formula Va and the compound of formula VIa are a compound of formula Vb and a compound of formula VIb, respectively:

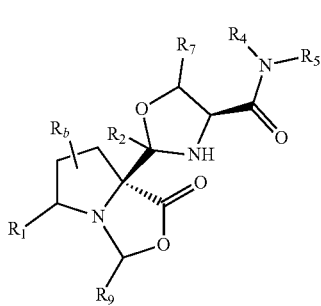

formula Vb

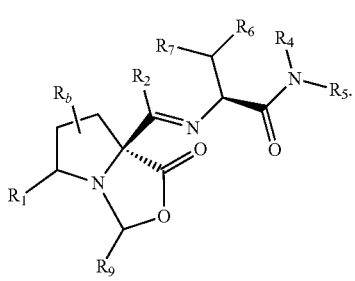

formula VIb

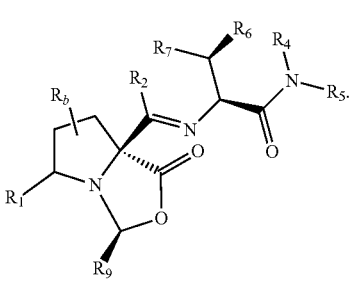

formula VId

Example embodiment 125: The compound of example embodiment 124, wherein the compound of formula Vb and the compound of formula VIb are a compound of formula Vc and a compound of formula VIc, respectively:

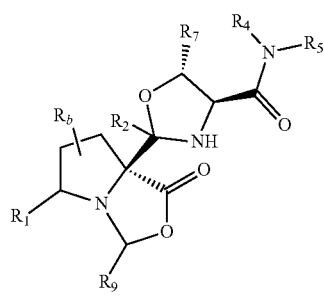

formula Vc

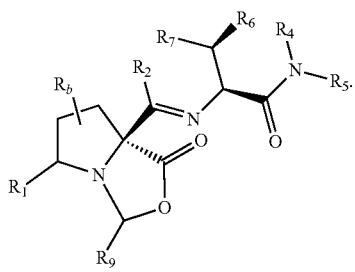

formula VIc

Example embodiment 126: The compound of example embodiment 125, wherein the compound of formula Vc and the compound of formula VIc are a compound of formula Vd and a compound of VId, respectively:

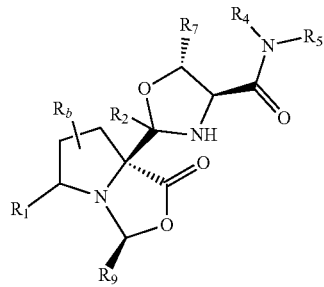

formula Vd

Example embodiment 127: The compound of any one of example embodiments 122 to 126, wherein $R_b$ is selected from H, halogen, cyano and C1-C6 alkyl;

$R_1$ is H or $C_1$-$C_6$ alkyl;

$R_2$ is H or $C_1$-$C_6$ alkyl;

$R_4$ and $R_5$ are independently selected from H and $C_1$-$C_6$ alkyl; or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from N—$C_1$-$C_6$ alkyl, O and S; and wherein the heterocyclyl is optionally substituted with one, two, or three substituents independently selected from halogen, cyano, $C_1$-$C_6$ alkyl, and $C_1$-$C_6$ alkoxy;

$R_6$ is selected from $C_1$-$C_6$ alkoxy, —OC(O)—$C_1$-$C_6$ alkyl, and —OC(O)phenyl;

$R_7$ is H or $C_1$-$C_6$ alkyl; and $R_9$ is —CCl$_3$.

Example embodiment 128: The compound of example embodiment 127, wherein $R_1$ and $R_2$ are H.

Example embodiment 129: The compound of example embodiment 127 or 128, wherein $R_9$ is CCl$_3$.

Example embodiment 130: The compound of any one of example embodiments 127 to 129, wherein each of $R_1$, $R_2$, $R_4$, and $R_5$ is H.

Example embodiment 131: The compound of any one of example embodiments 127 to 130, wherein $R_7$ is $C_1$-$C_6$ alkyl.

Example embodiment 132: The compound of example embodiment 131, wherein $R_7$ is methyl.

Example embodiment 133: The compound of example embodiment 122, wherein the compound of formula V is selected from the following compounds:

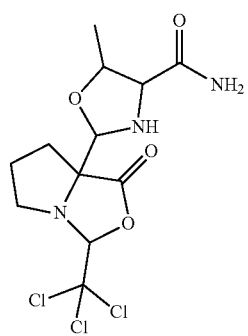

Compound E'

-continued

Compound E″

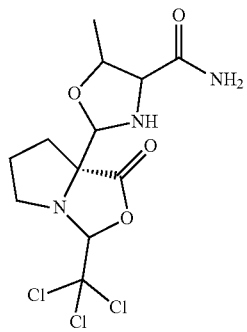

Compound E‴

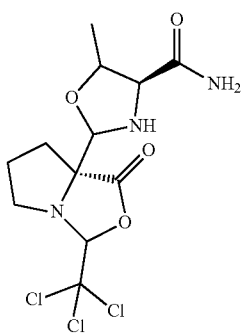

Compound E⁗

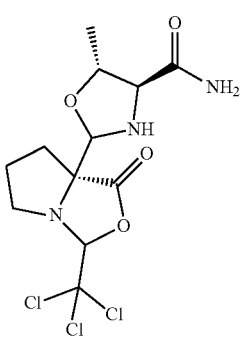

Compound E

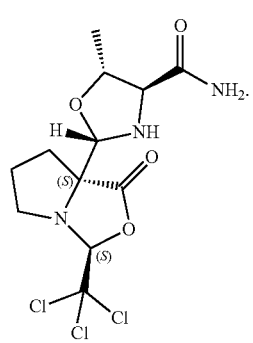

Example embodiment 134: The compound of example embodiment 133, wherein the compound of formula V is Compound E.

Additional embodiments of each of the aspects will be apparent from the following description, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples.

DETAILED DESCRIPTION

I. Definitions

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

As used herein, the term "alkenyl" refers to an unsaturated straight or branched hydrocarbon having at least one carbon-carbon double bond, such as a straight or branched group of 2-6 or 3-4 carbon atoms, referred to herein for example as $C_2$-$C_6$ alkenyl, and $C_3$-$C_4$ alkenyl, respectively. Exemplary alkenyl groups include, but are not limited to, vinyl, allyl, butenyl, pentenyl, etc.

The term "alkyl" as used herein refers to a saturated straight or branched hydrocarbon, such as a straight or branched group of 1 to 6, 1 to 4, or 1 to 3 carbon atoms, referred to herein as $C_1$-$C_6$ alkyl, $C_1$-$C_4$ alkyl, and $C_1$-$C_3$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkoxy" as used herein refers to a straight or branched alkyl group attached to an oxygen (alkyl-O—). Exemplary alkoxy groups include, but are not limited to, alkoxy groups of 1-6 or 2 to 6 carbon atoms, referred to herein as $C_1$-$C_6$ alkoxy, and $C_2$-$C_6$ alkoxy, respectively. Exemplary alkoxy groups include, but are not limited to methoxy, ethoxy, isopropoxy, etc.

The term "alkylene" as used herein refers to a bivalent saturated straight or branched hydrocarbon, such as a straight or branched group of 1 to 6, 1 to 4, or 1 to 3 carbon atoms, referred to herein as $C_1$-$C_6$ alkylene, $C_1$-$C_4$ alkylene, and $C_1$-$C_3$ alkylene, respectively. Exemplary alkylene groups include, but are not limited to, methylene (—$CH_2$—), ethylene (—$CH_2CH_2$—), propylene (—$CH_2CH_2CH_2$—), and isopropylene (—$CH_2CH(CH_3)$).

The term "alkynyl" as used herein refers to an unsaturated straight or branched hydrocarbon having at least one carbon-carbon triple bond, such as a straight or branched group of 2-6, or 3-6 carbon atoms, referred to herein as $C_2$-$C_6$ alkynyl, and $C_3$-$C_6$ alkynyl, respectively. Exemplary alkynyl groups include, but are not limited to, ethynyl, propynyl, butynyl, pentynyl, hexynyl, methylpropynyl, etc.

The term "cycloalkyl" as used herein refers to a monocyclic saturated or partially unsaturated (non-aromatic) hydrocarbon group of for example 3-6, or 4-6 carbons, referred to herein, e.g., as "$C_3$-$C_6$ cycloalkyl" or "$C_4$-$C_6$ cycloalkyl," and derived from a cycloalkane. Exemplary cycloalkyl groups include, but are not limited to, cyclohexane, cyclohexene, cyclopentane, cyclobutane, cyclopropane or cyclopentane.

The term "haloalkyl" as used herein refers to a saturated straight or branched alkyl groups, in which one or more hydrogen atoms of the alkyl group are replaced with one or more independently selected halogens. The term "haloalkyl" encompasses alkyl groups in which all of hydrogen atoms of the alkyl group are replaced independently selected halogens (sometimes referred to as "perhalo" alkyl groups. Exemplary haloalkyl groups include, but are not limited to, $CH_2F$, $CH_2CH_2C_1$, $CF_3$, $CHFCH_2Cl$.

The terms "heteroaryl" as used herein refers to a monocyclic aromatic 4-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine, and pyrimidine.

The terms "heterocyclyl" or "heterocyclic group" as used herein refer to saturated or partially unsaturated (but not aromatic) 4- to 7-membered ring structures, whose ring structures include one to three heteroatoms, such as nitrogen, oxygen, and sulfur. A heterocycle may be fused to one or more phenyl, partially unsaturated, or saturated rings. Examples of heterocyclyl groups include but are not limited to pyrrolidine, piperidine, morpholine, thiomorpholine, and piperazine.

As used herein, "isolated" means that a compound is substantially free of solvents and/or impurities.

In particular, with regards to intermediates (i.e. compounds other than compounds of Formula I or Compound A), "isolated" means substantially free of related impurities (e.g. impurities containing a substructure of the isolated intermediate whose molecular mass is at least 50% of the molecular mass of the intermediate) with no regard to solvents or non-related impurities such as inorganics, where "substantially free of related impurities" means that related impurities are together less than 20% of the weight of the intermediate. Thus, in some embodiments, the solvent content for isolated intermediates can be over 50 wt % when an intermediate is carried into the next step. Likewise, in some embodiments the inorganics content for isolated intermediates can also be over 50 wt % when an intermediate is carried into the next step.

Similarly, with regards to compounds of Formula I (e.g. Compound A), "isolated" means substantially free of all related and non-related impurities, solvents, and inorganics, where "substantially free of all related and non-related impurities, solvents, and inorganics" means that related impurities are together less than 3% by weight of the total weight of the obtained mass (including target compound, solvent, etc.), non-related impurities are together less than 3% by weight of the total weight of the obtained mass (including target compound, solvent, etc.), solvents (other than water) are less than 5% of the total weight of the obtained mass (including target compound, solvent, etc.), and inorganics are less than 3% by weight of the total weight of the obtained mass (including target compound, solvent, etc.). Thus, in some embodiments, water is often present at up to 5 wt % in isolated compounds of Formula I (e.g. Compound A). Similarly, in some embodiments, solvents are less than 0.5 wt % in isolated Compound A. In some embodiments Absolute purity on a water and solvent corrected basis is usually above 98 wt % in isolated compounds of Formula I (e.g. Compound A).

The term "hydrate" as used herein with reference to an aldehyde (e.g. "an aldehyde or hydrate thereof") refers to the hydrate form of the aldehyde:

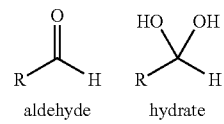

aldehyde    hydrate

In particular, in some embodiments, when an aldehyde is contacted with another compound (e.g. in a chemical reaction), the aldehyde can originally be in its hydrate form, which can, for example have better handling properties than the aldehyde form (e.g. chloral hydrate, $C_3CH(OH)_2$, can be easier to handle that chloral itself, $C_3CHO$, because chloral hydrate is crystalline and not subject to the possible polymerization that chloral can be subject to). Accordingly, even if the species in a chemical reaction that reacts with the compound it is contacted with is an aldehyde, the original reagent used in the reaction can be the hydrate form of the aldehyde which can be in equilibrium with the aldehyde form (and said equilibrium can be shifted towards the aldehyde by removing water, for example using molecular sieves, co-distillation with acetonitrile or other solvents, and/or other water removal methods identifiable to a skilled person).

The term "contacting" as used herein refers to bringing two or more substances (e.g. compounds) into sufficiently close proximity such that chemical reaction of the molecules of the two substances can occur. In some embodiments, the contacting of the two substances occurs when the two substances are dissolved in a solvent. In some embodiments, a first substance is contacted with a second substance by dissolving and/or suspending the first substance in a solvent (e.g. a liquid solvent) and either i) adding the second substance (e.g. neat or in a solvent such as a liquid solvent) to the solution or suspension of the first substance, or ii) adding the solution or suspension of the first substance to the second substance (which itself could be dissolved and/or suspended in a solvent) thereby allowing the molecules of the two substances to react.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(.+−.)", or "+/−", or "±" in nomenclature, but the skilled artisan will recognize that a structure may denote a chiral center implicitly.

Individual enantiomers and diastereoisomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. For examples, see Carreira and Kvaemo, *Classics in Stereoselective Synthesis*, Wiley-VCH: Weinheim, 2009.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm. Similarly, if a range such as $C_1$-$C_6$ alkyl is stated, it is intended that $C_1$ alkyl, $C_2$ alkyl, $C_3$ alkyl, $C_4$ alkyl, $C_5$ alkyl, and $C_6$ alkyl are also explicitly disclosed.

The singular forms "a," "an," and "the" include plural referents unless the context clearly dictates otherwise. Thus, for example, reference to a "liposome" includes a single liposome as well as two or more of the same or different liposomes, reference to an "excipient" includes a single excipient as well as two or more of the same or different excipients, and the like.

The close-ended term "consist essentially of" or "consist of" is within the scope of the open-ended term "comprising," "containing," or "including".

II. Processes

A. Preparation of Compound of Formula I

In one aspect, a process of producing a compound of formula I or a pharmaceutically acceptable salt thereof is provided. The process comprises contacting a compound of formula II and a coupling agent in an organic solvent to obtain a compound of formula I or a pharmaceutically acceptable salt thereof, wherein the coupling agent comprises an art recognized agent for coupling an amine and carboxylic acid to form an amide bond:

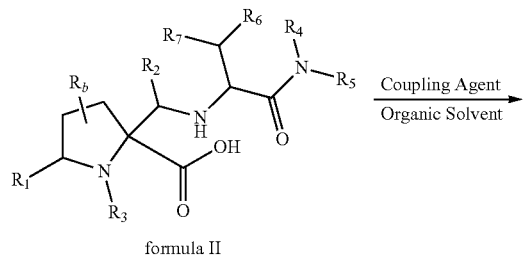

formula II

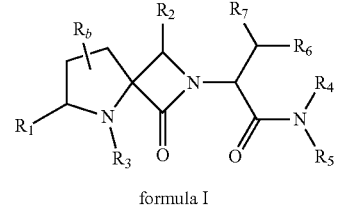

formula I wherein:
$R_b$ is selected from H, halogen, cyano and $C_1$-$C_6$ alkyl;
$R_1$ is H or $C_1$-$C_6$ alkyl;
$R_2$ is H or $C_1$-$C_6$ alkyl;
$R_3$ is selected from $C_1$-$C_6$ alkyl and $C(O)OR_8$;
$R_8$ is selected from $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, and —$CH_2$—$C_3$-$C_{10}$ cycloalkyl, wherein $C_3$-$C_{10}$ cycloalkyl is optionally substituted with one, two, or three groups selected from $C_1$-$C_3$ alkyl;
$R_4$ and $R_5$ are independently selected from H, $C_1$-$C_6$ alkyl, X, and —$C_1$-$C_6$ alkylene-X, wherein X is selected from:
(i) $C_3$-$C_6$ cycloalkyl;
(ii) heteroaryl including from 5 to 6 ring atoms wherein one, two, or three of the ring atoms are independently selected from N, NH, N($C_1$-$C_3$ alkyl), O, and S;
(iii) heterocyclyl including from three to six ring atoms wherein 1, 2, or 3 of the ring atoms are independently selected from N, NH, N($C_1$-$C_3$alkyl), O, and S; and
(iv) phenyl;
wherein $C_3$-$C_6$ cycloalkyl, heterocyclyl, heteroaryl, and phenyl are each optionally substituted with one, two, or three substituents independently selected halogen, cyano, $C_1$-$C_6$ alkyl, hydroxyl, and $C_1$-$C_6$ alkoxy;
or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from N—$C_1$-$C_6$ alkyl, O and S; and wherein the heterocyclyl is optionally substituted with one, two, or three substituents independently selected from halogen, cyano, $C_1$-$C_6$ alkyl, and $C_1$-$C_6$ alkoxy;
$R_6$ is selected from —OH, $C_1$-$C_6$ alkoxy, —OC(O)—$C_1$-$C_6$ alkyl, and —OC(O)phenyl; and
$R_7$ is H or $C_1$-$C_6$ alkyl.

In some embodiments, the coupling agent comprises a carbodiimide optionally together with 1-hydroxybenzotriazole (HOBt). In some embodiments, the coupling agent comprises a carbodiimide selected from dicyclohexylcarbodiimide (DCC), diisopropylcarbodiimide (DIC), and ethyl-(N',N'-dimethylamino)propylcarbodiimide hydrochloride (EDC).

In some embodiments, the coupling agent comprises (Benzotriazol-1-yloxy)tris(dimethylamino)phosphonium hexafluorophosphate (BOP), (Benzotriazol-1-yloxy)tripyrrolidinophosphonium hexafluorophosphate (PyBOP), (7-Azabenzotriazol-1-yloxy)tripyrrolidinophosphonium hexafluorophosphate (PyAOP), Bromotripyrrolidinophosphonium hexafluorophosphate (PyBrOP), Bis(2-oxo-3-oxazolidinyl)phosphinic chloride (BOP—Cl), O-(Benzotriazol-1-yl)-N,N,N',N'-tetramethyluronium hexafluorophosphate (HBTU), O-(Benzotriazol-1-yl)-N,N,N',N'-tetramethyluronium tetrafluoroborate (TBTU), O-(7-Azabenzotriazol-1-yl)-N,N,N',N'-tetramethyluronium hexafluorophosphate (HATU), O-(7-Azabenzotriazol-1-yl)-N,N,N',N'-tetramethyluronium tetrafluoroborate (TATU), O-(6-Chlorobenzotriazol-1-yl)-N,N,N',N'-tetramethyluronium hexafluorophosphate (HCTU), O-[(Ethoxycarbonyl)cyanomethylenamino]-N,N,N',N'-tetramethyluronium tetrafluoroborate (TOTU), (1-Cyano-2-ethoxy-2-oxoethylidenaminooxy)dimethylamino-morpholino-carbenium hexafluorophosphate (COMU), O—(N-Suc-cinimidyl)-1,1,3,3-tetramethyl-uronium tetrafluoroborate (TSTU), O-(5-Norbornene-2,3-dicarboximido)-N,N,N',N'-tetramethyluronium tetrafluoroborate (TNTU), O-(1,2-Dihydro-2-oxo-1-pyridyl-N,N,N',N'-tetramethyluronium tetrafluoroborate (TPTU), N,N,N',N'-Tetramethyl-O-(3,4-dihydro-4-oxo-1,2,3-benzotriazin-3-yl)uranium tetrafluoroborate (TDBTU), N,N,N',N'-Tetramethylchloroformamidinium Hexafluorophosphate (TCFH), 3-(Diethylphosphoryloxy)-1,2,3-benzotriazin-4(3H)-one (DEPBT), or Carbonyldiimidazole (CDI).

In some embodiments, the coupling agent is a di-$C_1$-$C_6$ alkyl halophosphate (such as a di-$C_1$-$C_6$ alkyl chlorophosphate), a dialkyl phosphinic halide, or propanephosphonic acid anhydride (e.g. T3P®). In some embodiments, the coupling agent comprises diethyl chlorophosphate.

In some embodiments, the coupling agent is used together with an organic base. In some embodiments, the organic base comprises an amine. In some embodiments, the organic base comprises triethyl amine, N,N-Diisopropylethylamine (DIPEA), or 4-Dimethylaminopyridine (DMAP). In some embodiments, the organic base comprises triethyl amine.

In some embodiments, the process is carried out in an organic solvent comprising dimethylformamide (DMF), dimethyl sulfoxide (DMSO), N-Methyl-2-pyrrolidone (NMP), acetonitrile (MeCN), dichloromethane (DCM), tetrahydrofuran (THF), or 2-methyltetrahydrofuran (2-MeTHF). In some embodiments, the solvent comprises THF.

In some embodiments, the process further comprises contacting a compound of formula IV with a base in a solvent to obtain a compound of formula III, wherein the compound of formula III is subsequently subjected to alkylating agent (such as alkyl halide) or carbamating agent (such as di-$R_8$ dicarbonate, for example $BOC_2O$) to obtain a compound of formula II, wherein $R_b$, $R_1$, $R_2$, $R_3$, $R_4$, $R_5$, $R_6$, and $R_7$ are the same as described above, and $R_9$ is —$CCl_3$:

In some embodiments, the base comprises an amine. In some embodiments, the base comprises an amine selected from triethyl amine or DIPEA.

In some embodiments, the solvent is an aqueous solvent. In some embodiments, the aqueous solvent is a mixture of water with acetonitrile or a mixture of water with THF (or with 2-MeTHF). In other embodiments, the aqueous solvent is a mixture of water with methanol, a mixture of water with ethanol, a mixture of water with isopropanol, a mixture of water with DMF, or a mixture of water with DMSO.

In some embodiments, the process further comprises contacting a compound of formula VII with an amine of formula VIII to obtain a condensed product of formula V or VI, which is subsequently contacted with a reducing compound to obtain a compound of formula IV, wherein $R_b$, $R_1$, $R_2$, $R_3$, $R_4$, $R_5$, $R_6$, $R_7$, and $R_9$ are the same as described above:

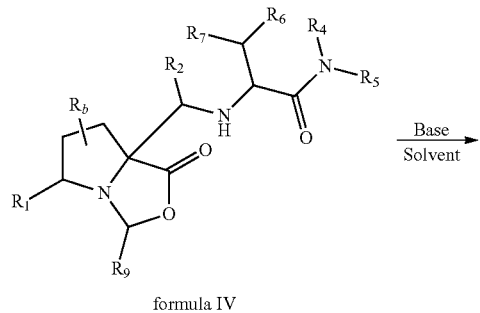

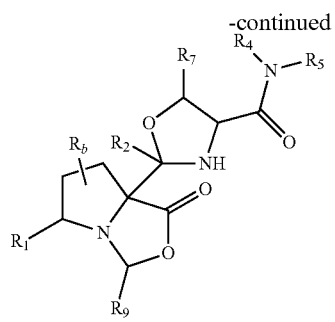

formula V
(when R$_6$ in formula VIII is OH)

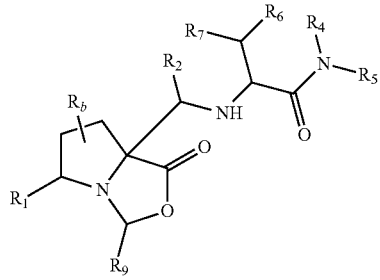

formula IV

In some embodiments, the solvent for the condensation reaction comprises dichloromethane. In some embodiments, the solvent for the condensation reaction comprises toluene. In some embodiments, the solvent comprises DMF. In some embodiments, the solvent comprises THF. In some embodiments, the solvent comprises 2-MeTHF. In some embodiments, the solvent comprises DMF. In some embodiments, the solvent comprises acetonitrile.

In some embodiments, the reducing agent comprises a boron hydride. In some embodiments, the reducing agent comprises a boron hydride selected from sodium borohydride, lithium borohydride, calcium borohydride, magnesium borohydride, sodium triacetoxyborohydride (NaBH(OAc)$_3$), NBu$_4$BH$_4$, NaCNBH$_3$, and NMe$_4$BH(OAc)$_3$. In some embodiments, the reducing agent comprises sodium triacetoxyborohydride (NaBH(OAc)$_3$).

In some embodiments, before contacting it with the reducing agent, the compound of formula V or VI is not isolated.

In some embodiments, the process further comprises contacting the compound of formula IX with a base known in the art to deprotonate the α carbon next to a carbonyl (CO) in a solvent (e.g. lithium diisopropylamide (LDA), potassium tert-butoxide (KOtBu), and others identifiable to a skilled person upon a reading of the present disclosure), which is subsequently followed by addition of R$_2$C(O)OR (R is methyl, ethyl, phenyl, —CH$_2$CF$_3$, or —CH$_2$CN) to obtain the compound of formula VII:

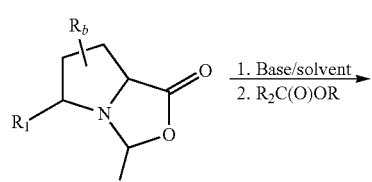

formula IX

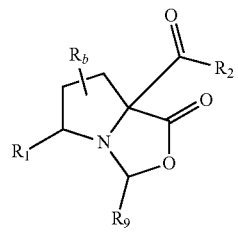

formula VII

In some embodiments, the deprotonation is conducted at a temperature below 0° C., such as at a temperature of −80 to −20° C.

In some embodiments, the base comprises lithium diisopropylamide. In some embodiments, the base is potassium tert-butoxide.

In some embodiments, the solvent comprises toluene with methyl tert-butyl ether (MTBE) optionally added. In some embodiments, the solvent is MTBE. In some embodiments, the solvent comprises THF, optionally mixed with toluene or MTBE. In some embodiments, the solvent comprises 2-MeTHF, optionally mixed with toluene or MTBE.

In some embodiments, R$_2$C(O)OR is added to the deprotonated formula IX at a temperature below 0° C., such as at a temperature of −80 to −20° C., for example about −60° C.

In some embodiments, the process further comprises contacting a compound of formula X with an aldehyde R$_9$CHO, or a hydrate thereof, to obtain a compound of formula IX:

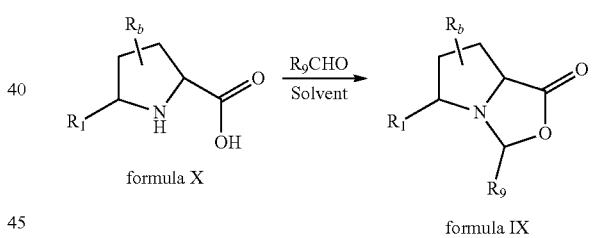

formula X → formula IX

In some embodiments, the solvent used to obtain the compound of formula IX comprises THF, 2-MeTHF, acetonitrile, toluene, dichloromethane, chloroform, or MTBE.

In some embodiments, the compound of formula I is a compound of formula Ia:

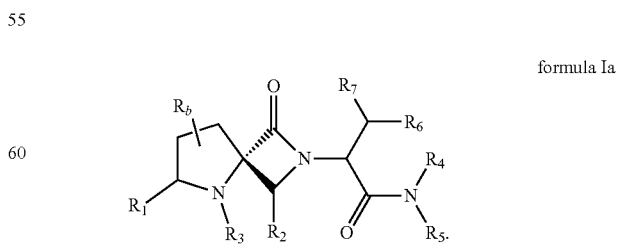

formula Ia

In some embodiments, the compound of formula Ia is a compound of formula Ib:

formula Ib

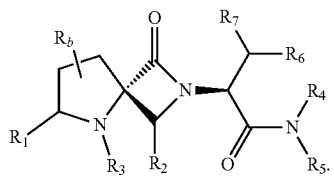

In some embodiments, the compound of formula Ib is a compound of formula Ic:

formula Ic

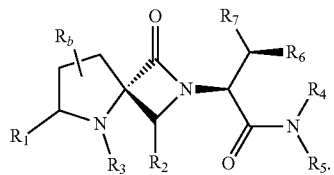

In some embodiments, the compound of formula II is a compound of formula IIa:

formula IIa

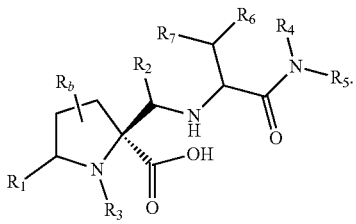

In some embodiments, the compound of formula IIa is a compound of formula IIb:

formula IIb

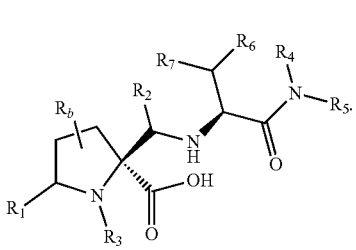

In some embodiments, the compound of formula IIa is a compound of formula IIc:

formula IIc

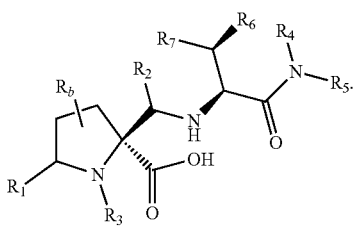

In some embodiments, the compound of formula III is a compound of formula IIIa:

formula IIIa

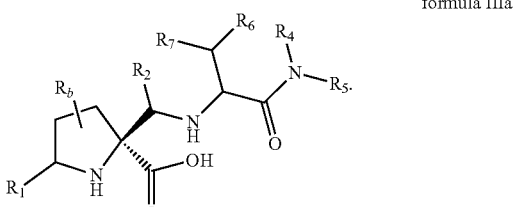

In some embodiments, the compound of formula IIa is a compound of formula IIIb:

formula IIIb

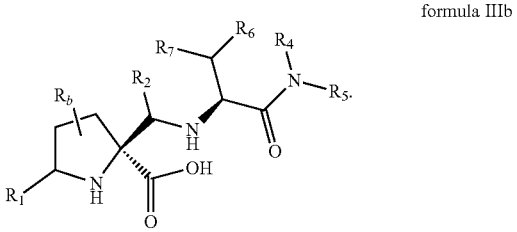

In some embodiments, the compound of formula IIIa is a compound of formula IIIc:

formula IIIc

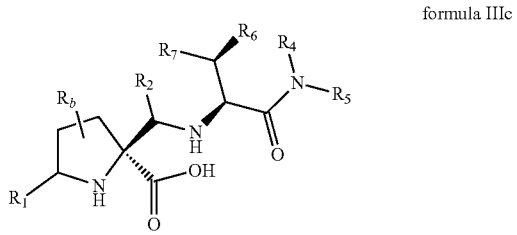

In some embodiments, the compound of formula IV is a compound of formula IVa:

formula IVa

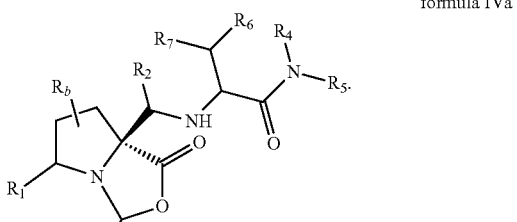

In some embodiments, the compound of formula IVa is a compound of formula IVb:

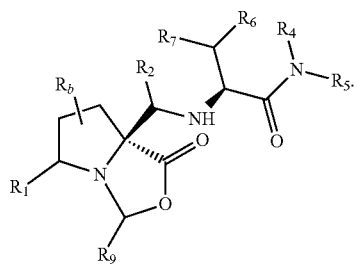
formula IVb

In some embodiments, the compound of formula IVb is a compound of formula IVc:

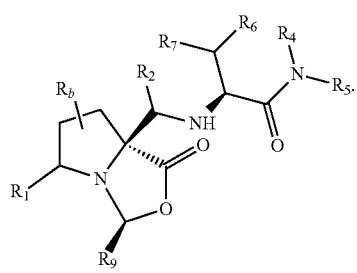
formula IVc

In some embodiments, the compound of formula IVb is a compound of formula IVd:

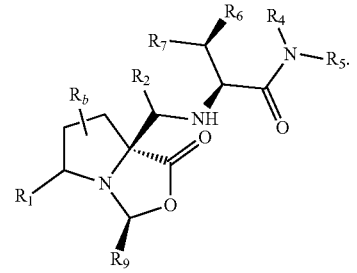
formula IVd

In some embodiments, the compound of formula V and the compound of formula VI are a compound of formula Va and a compound of formula VIa, respectively;

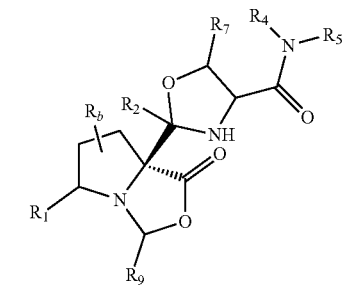
formula Va

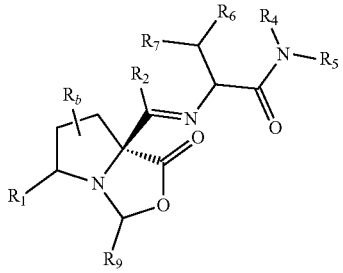
formula IVa

In some embodiments, the compound of formula Va and the compound of formula VIa are a compound of formula Vb and a compound of formula VIb, respectively:

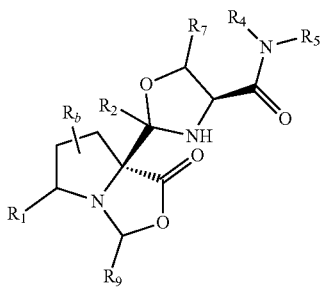
formula Vb

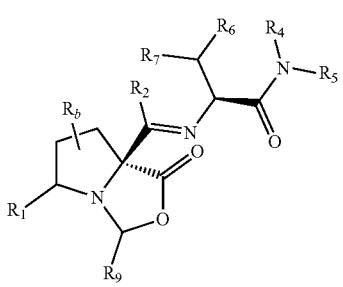
formula IVb

In some embodiments, the compound of formula Vb and the compound of formula VIb are a compound of formula Vc and a compound of formula VIc, respectively:

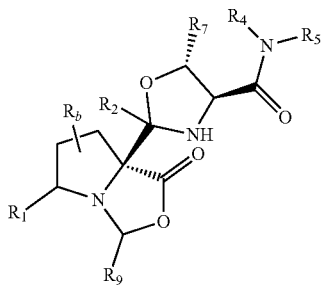
formula Vc

-continued

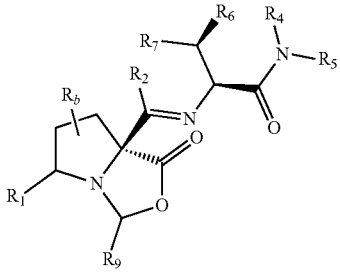
formula IVc

In some embodiments, the compound of formula Vc and the compound of formula VIc are a compound of formula Vd and a compound of VId, respectively:

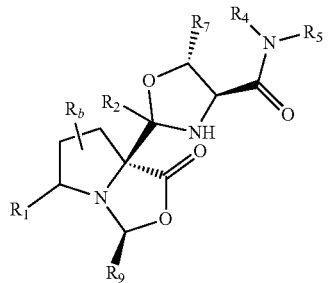
formula Vd

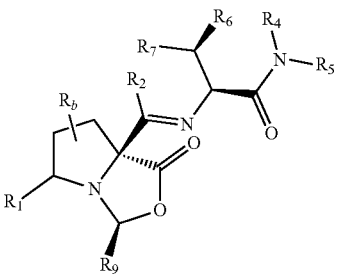
formula IVd

In some embodiments, the compound of formula VII is a compound of formula VIIa:

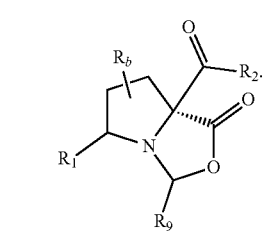
formula VIIa

In some embodiments, the compound of formula VIIa is a compound of formula VIIb:

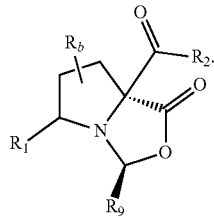
formula VIIb

In some embodiments, the compound of formula VIII is a compound of formula VIIIa:

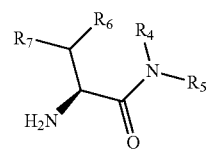
formula VIIIa

In some embodiments, the compound of formula VIIIa is a compound of formula VIIIb:

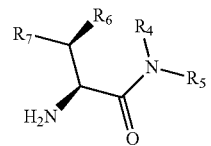
formula VIIIb

In some embodiments, the compound of formula IX is a compound of formula IXa:

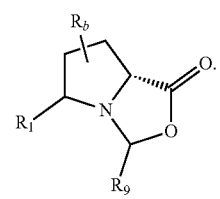
formula IXa

In some embodiments, the compound of formula IXa is a compound of formula IXb:

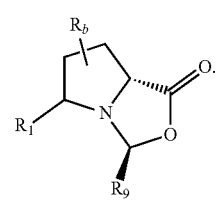
formula IXb

In some embodiments, the compound of formula X is a compound of formula Xa:

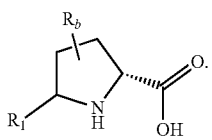

formula Xa

In some embodiments, in each of formulae I to X (including formulae thereof wherein with the chiral center(s) is defined), wherein applicable, $R_b$ is selected from H, halogen, cyano and $C_1$-$C_6$ alkyl;
$R_1$ is H or $C_1$-$C_6$ alkyl;
$R_2$ is H or $C_1$-$C_6$ alkyl;
$R_3$ is selected from $C_1$-$C_6$ alkyl and C(O)OR$_8$;
$R_8$ is selected from $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, and —CH$_2$—$C_3$-$C_{10}$ cycloalkyl, wherein $C_3$-$C_{10}$ cycloalkyl is optionally substituted with one, two, or three groups selected from $C_1$-$C_3$ alkyl;
$R_4$ and $R_5$ are independently selected from H and $C_1$-$C_6$ alkyl; or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from N—$C_1$-$C_6$ alkyl, O and S; and wherein the heterocyclyl is optionally substituted with one, two, or three substituents independently selected from halogen, cyano, $C_1$-$C_6$ alkyl, and $C_1$-$C_6$ alkoxy;
$R_6$ is selected from —OH, $C_1$-$C_6$ alkoxy, —OC(O)—$C_1$-$C_6$ alkyl, and —OC(O)phenyl; $R_7$ is H or $C_1$-$C_6$ alkyl; and
$R_9$ is selected from CCl$_3$.

In some embodiments, in each of formulae I to X (including formulae thereof wherein the chiral center(s) is defined), where applicable, $R_1$ and $R_2$ are H.

In some embodiments, in each of formulae I to X (including formulae thereof wherein with the chiral center(s) is defined), where applicable, each of $R_1$, $R_2$, $R_4$, and $R_5$ is H.

In some embodiments, in each of formulae I to VIII (including formulae thereof wherein with the chiral center(s) is defined), $R_6$ is OH.

In some embodiments, in each of formulae I to VIII (including formulae thereof wherein with the chiral center(s) is defined), $R_7$ is $C_1$-$C_6$ alkyl, such as methyl.

In some embodiments, in each of formula I and II (including formulae thereof wherein with the chiral center(s) is defined), $R_1$ is OC(O)R$_8$, wherein $R_8$ is $C_1$-$C_6$ alkyl, such as tertiary butyl.

In some embodiments, the compound of formula II is selected from the following compounds:

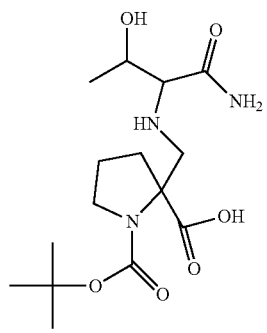

Compound B'

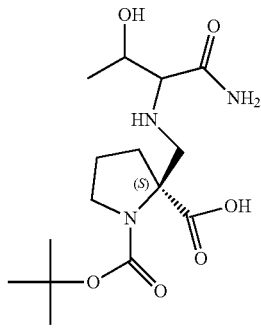

Compound B''

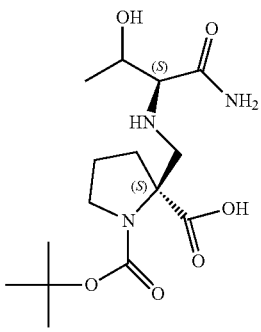

Compound B'''

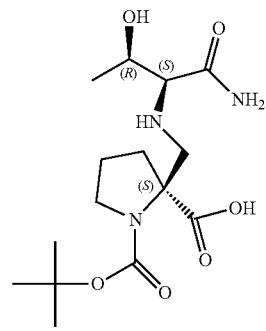

Compound B

In some embodiments, the compound of formula III is selected from the following compounds:

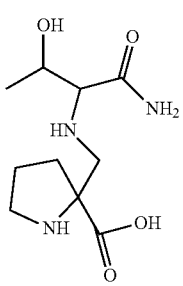

Compound C'

-continued
Compound C''
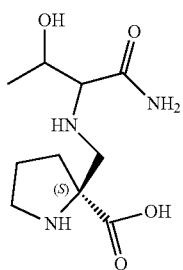
Compound C'''
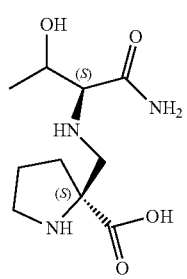
Compound C
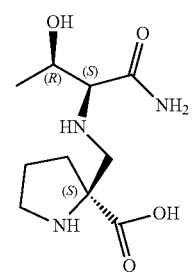
In some embodiments, the compound of formula IV is selected from the following compounds:
Compound D'
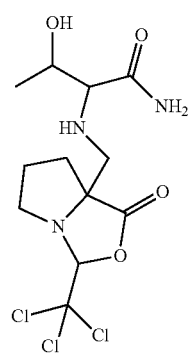
-continued
Compound D''
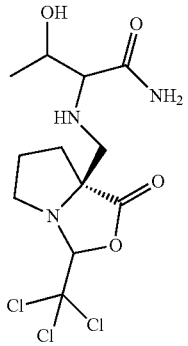
Compound D'''
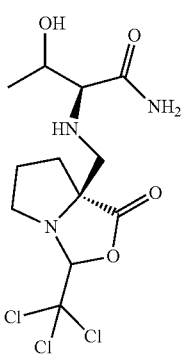
Compound D''''
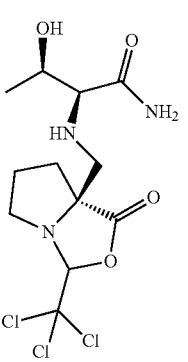
Compound D
In some embodiments, the compound of formula V are selected from the following compounds:

Compound E'

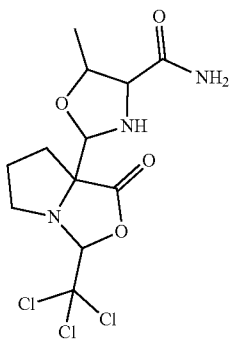

Compound E''

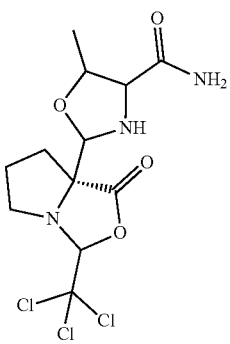

Compound E'''

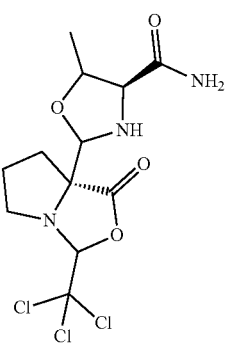

Compound E''''

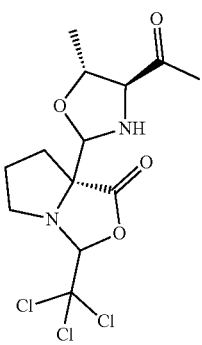

Compound E

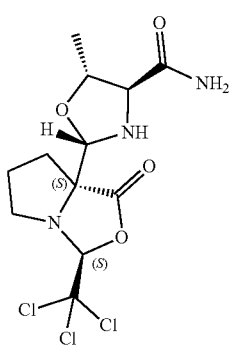

B. Preparation of Compound A

In another aspect, a process of producing tert-butyl (S)-2-((2S,3R)-1-amino-3-hydroxy-1-oxobutan-2-yl)-1-oxo-2,5-diazaspiro[3.4]octane-5-carboxylate ("Compound A") is provided. This process comprises contacting Compound B with a coupling agent in an organic solvent to obtain Compound A, wherein the coupling agent comprises an art recognized agent for coupling an amine and carboxylic acid to form an amide bond:

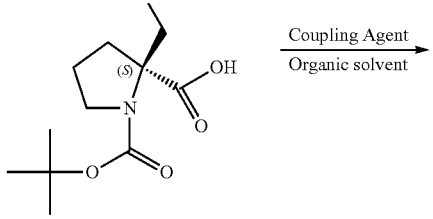

Compound B

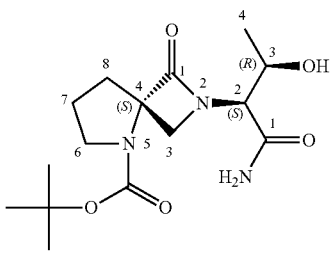

Compound A and wherein Compound B is obtained by contacting Compound C with di-tert-butyl dicarbonate (BOC₂O) in a solvent:

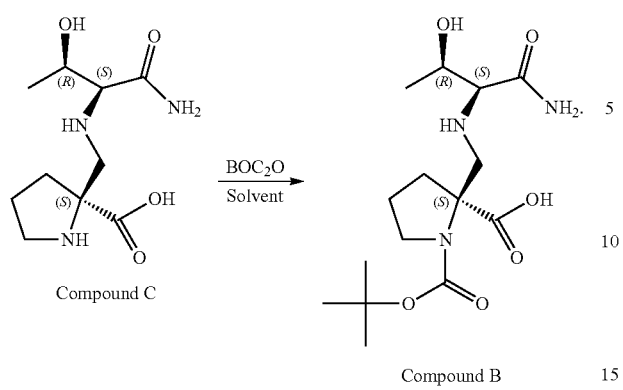

Compound C → Compound B (BOC₂O, Solvent)

(NMP), acetonitrile (MeCN), dichloromethane (DCM), tetrahydrofuran (THF), or 2-methyltetrahydrofuran (2-MeTHF). In some embodiments, the solvent comprises THF In some embodiments, the solvent used to prepare Compound B comprises acetonitrile, methanol, ethanol, isopropanol, MTBE, toluene, acetone, $CH_2Cl_2$, THF, 2-MeTHF, water, and mixtures thereof. In some embodiments, an amine, such as triethyl amine is present in the reaction to prepare Compound B.

In some embodiments, the process further comprises contacting Compound D with a base in a solvent to obtain Compound C:

In some embodiments, the coupling agent comprises a carbodiimide optionally together with 1-hydroxybenzotriazole (HOBt). In some embodiments, the coupling agent comprises a carbodiimide selected from dicyclohexylcarbodiimide (DCC), diisopropylcarbodiimide (DIC), and ethyl-(N',N'-dimethylamino)propylcarbodiimide hydrochloride (EDC).

In some embodiments, the coupling agent comprises (Benzotriazol-1-yloxy)tris(dimethylamino)phosphonium hexafluorophosphate (BOP), (Benzotriazol-1-yloxy)tripyrrolidinophosphonium hexafluorophosphate (PyBOP), (7-Azabenzotriazol-1-yloxy)tripyrrolidinophosphonium hexafluorophosphate (PyAOP), Bromotripyrrolidinophosphonium hexafluorophosphate (PyBrOP), Bis(2-oxo-3-oxazolidinyl)phosphinic chloride (BOP—Cl), O-(Benzotriazol-1-yl)-N,N,N',N'-tetramethyluronium hexafluorophosphate (HBTU), O-(Benzotriazol-1-yl)-N,N,N',N'-tetramethyluronium tetrafluoroborate (TBTU), O-(7-Azabenzotriazol-1-yl)-N,N,N',N'-tetramethyluronium hexafluorophosphate (HATU), O-(7-Azabenzotriazol-1-yl)-N,N,N',N'-tetramethyluronium tetrafluoroborate (TATU), O-(6-Chlorobenzotriazol-1-yl)-N,N,N',N'-tetramethyluronium hexafluorophosphate (HCTU), O-[(Ethoxycarbonyl)cyanomethylenamino]-N,N,N',N'-tetra methyluronium tetrafluoroborate (TOTU), (1-Cyano-2-ethoxy-2-oxoethylidenaminooxy)dimethylamino-morpholino-carbenium hexafluorophosphate (COMU), O—(N-Suc-cinimidyl)-1,1,3,3-tetramethyl-uronium tetrafluoroborate (TSTU), O-(5-Norbornene-2,3-dicarboximido)-N,N,N',N'-tetramethyluronium tetrafluoroborate (TNTU), O-(1,2-Dihydro-2-oxo-1-pyridyl-N,N,N',N'-tetramethyluronium tetrafluoroborate (TPTU), N,N,N',N'-Tetramethyl-O-(3,4-dihydro-4-oxo-1,2,3-benzotriazin-3-yl)uranium tetrafluoroborate (TDBTU), N,N,N',N'-Tetramethylchloroformamidinium Hexafluorophosphate (TCFH), 3-(Diethylphosphoryloxy)-1,2,3-benzotriazin-4(3H)-one (DEPBT), or Carbonyldiimidazole (CDI).

In some embodiments, the coupling agent is a di-$C_1$-$C_6$ alkyl halophosphate (such as a di-$C_1$-$C_6$ alkyl chlorophosphate), a dialkyl phosphinic halide, or propanephosphonic acid anhydride (e.g. T3P®). In some embodiments, the coupling agent comprises diethyl chlorophosphate.

In some embodiments, the coupling agent is used together with an organic base. In some embodiments, the organic base comprises an amine. In some embodiments, the organic base comprises triethyl amine, N,N-Diisopropylethylamine (DIPEA), or 4-Dimethylaminopyridine (DMAP). In some embodiments, the organic base comprises triethyl amine.

In some embodiments, the process is carried out in an organic solvent comprising dimethylformamide (DMF), dimethyl sulfoxide (DMSO), N-Methyl-2-pyrrolidone

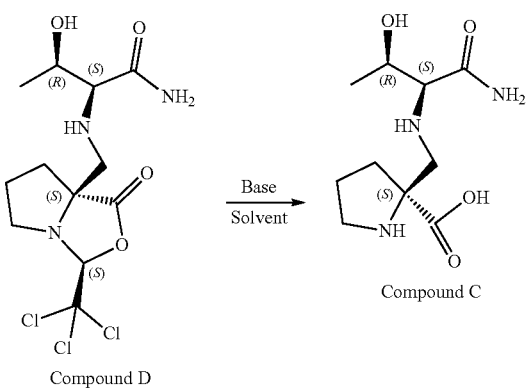

Compound D → Compound C (Base, Solvent)

In some embodiments, the base comprises an amine. In some embodiments, the base comprises an amine selected from triethyl amine and DIPEA.

In some embodiments, the solvent is an aqueous solvent. In some embodiments, the aqueous solvent is a mixture of water with acetonitrile or a mixture of water with THF (or with 2-MeTHF). In other embodiments, the aqueous solvent is a mixture of water with methanol, a mixture of water with ethanol, a mixture of water with isopropanol, a mixture of water with DMF, or a mixture of water with DMSO.

In some embodiments, the process further comprises contacting Compound F with Compound G to obtain a condensed product Compound E, which is subsequently contacted with a reducing compound to obtain Compound D:

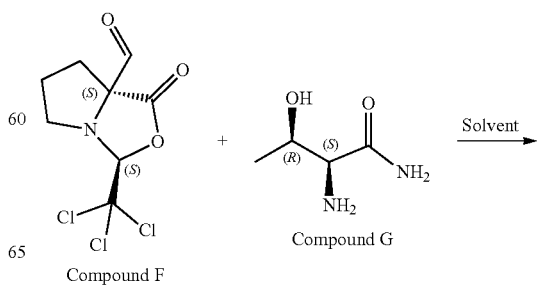

Compound F + Compound G → (Solvent)

-continued

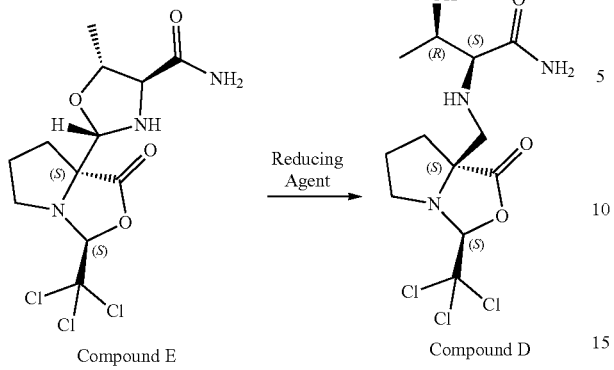

Compound E → Reducing Agent → Compound D

In some embodiments, the solvent for the condensation reaction comprises dichloromethane. In some embodiments, the solvent for the condensation reaction comprises toluene. In some embodiments, the solvent comprises DMF. In some embodiments, the solvent comprises THF. In some embodiments, the solvent comprises 2-MeTHF. In some embodiments, the solvent comprises DMF. In some embodiments, the solvent comprises acetonitrile.

In some embodiments, the reducing agent comprises a boron hydride. In some embodiments, the reducing agent comprises a boron hydride selected from sodium borohydride, lithium borohydride, calcium borohydride, magnesium borohydride, sodium triacetoxyborohydride (NaBH(OAc)$_3$), NBu$_4$BH$_4$, NaCNBH$_3$, and NMe$_4$BH(OAc)$_3$.

In some embodiments, before contacting it with the reducing agent, Compound E is not isolated.

In some embodiments, the process further comprises contacting Compound H with a base known in the art to deprotonate the α carbon next to a carbonyl (CO) in a solvent, which is subsequently followed by addition of HC(O)OR (R is methyl, ethyl, phenyl, —CH$_2$CF$_3$, or —CH$_2$CN) to obtain Compound F:

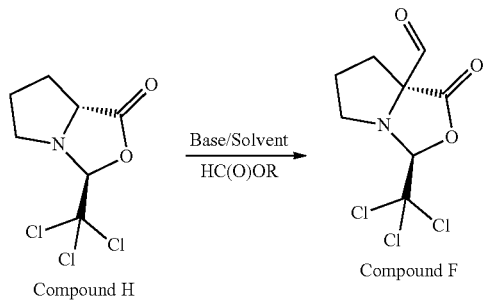

Compound H → Base/Solvent, HC(O)OR → Compound F

In some embodiments, the deprotonation is conducted at a temperature below 0° C., such as at a temperature of −80 to −20° C., for example about −45° C.

In some embodiments, the base comprises lithium diisopropylamide. In some embodiments, the base is potassium tert-butoxide.

In some embodiments, the solvent comprises toluene with methyl tert-butyl ether (MTBE) optionally added. In some embodiments, the solvent is MTBE. In some embodiments, the solvent comprises THF, optionally mixed with toluene or MTBE. In some embodiments, the solvent comprises 2-MeTHF, optionally mixed with toluene or MTBE.

In some embodiments, HC(O)OR is added to the deprotonated Compound H at a temperature below 0° C., such as at a temperature of −80 to −20° C., for example about −60° C.

In some embodiments, the process further comprises contacting D-proline with chloral to obtain Compound H:

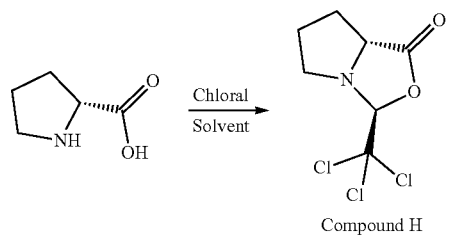 [SMILES: O=C(O)[C@H]1CCCN1 ; "Solvent" ; O=C1O[C@@H](C(Cl)(Cl)Cl)N2CCC[C@H]12]

→ Chloral, Solvent → Compound H

In some embodiments, the solvent used to obtain Compound H comprises THF, 2-MeTHF, acetonitrile, toluene, dichloromethane, chloroform, or MTBE. In some embodiments, the solvent used to obtain Compound H comprises acetonitrile.

III. Intermediates

A. Compound of Formula II

In one aspect, a compound that is useful in the process of producing the diazaspiro lactam compound of formula I is provided. The compound is a compound of formula II:

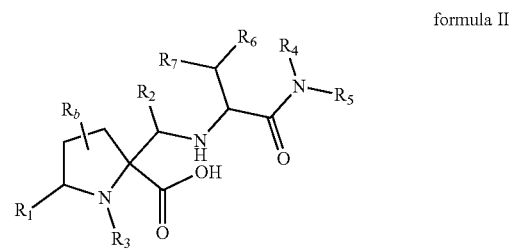

formula II wherein:
R$_b$ is selected from H, halogen, cyano and C$_1$-C$_6$ alkyl;
R$_1$ is H or C$_1$-C$_6$ alkyl;
R$_2$ is H or C$_1$-C$_6$ alkyl;
R$_3$ is selected from C$_1$-C$_6$ alkyl and C(O)OR$_8$;
R$_8$ is selected from C$_1$-C$_6$ alkyl, C$_1$-C$_6$ haloalkyl, C$_2$-C$_6$ alkenyl, C$_2$-C$_6$ alkynyl, C$_3$-C$_{10}$ cycloalkyl, and —CH$_2$—C$_3$-C$_{10}$ cycloalkyl, wherein C$_3$-C$_{10}$ cycloalkyl is optionally substituted with one, two, or three groups selected from C$_1$-C$_3$ alkyl;
R$_4$ and R$_5$ are independently selected from H, C$_1$-C$_6$ alkyl, X, and C$_1$-C$_6$ alkylene-X, wherein X is selected from:
(i) C$_3$-C$_6$ cycloalkyl;
(ii) heteroaryl including from 5 to 6 ring atoms wherein one, two, or three of the ring atoms are independently selected from N, NH, N(C$_1$-C$_3$ alkyl), O, and S;
(iii) heterocyclyl including from three to six ring atoms wherein 1, 2, or 3 of the ring atoms are independently selected from N, NH, N(C$_1$-C$_3$ alkyl), O, and S; and
(iv) phenyl;
wherein C$_3$-C$_6$ cycloalkyl, heterocyclyl, heteroaryl, and phenyl are each optionally substituted with one, two, or three substituents independently selected halogen, cyano, $C_1$-$C_6$ alkyl, hydroxyl, and $C_1$-$C_6$ alkoxy;

or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from N—$C_1$-$C_6$ alkyl, O and S; and wherein the heterocyclyl is optionally substituted with one, two, or three substituents independently selected from halogen, cyano, $C_1$-$C_6$ alkyl, and $C_1$-$C_6$ alkoxy;

$R_6$ is selected from —OH, $C_1$-$C_6$ alkoxy, —OC(O)—$C_1$-$C_6$ alkyl, and —OC(O)phenyl; and $R_7$ is H or $C_1$-$C_6$ alkyl.

In some embodiments, the compound of formula II is a compound of formula IIa:

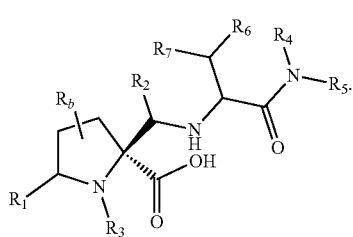

formula IIa

In some embodiments, the compound of formula IIa is a compound of formula IIb:

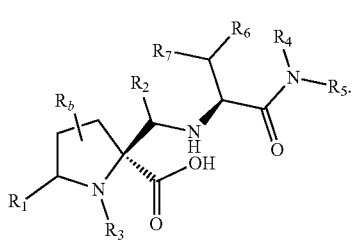

formula IIb

In some embodiments, the compound of formula IIb is a compound of formula IIc:

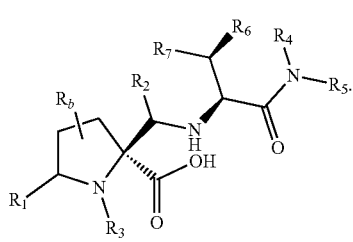

formula IIc

In some embodiments, in each of formulae II, IIa, IIb, and IIc:

$R_b$ is selected from H, halogen, cyano and $C_1$-$C_6$ alkyl;
$R_1$ is H or $C_1$-$C_6$ alkyl;
$R_2$ is H or $C_1$-$C_6$ alkyl;
$R_3$ is selected from $C_1$-$C_6$ alkyl and C(O)OR$_8$;
$R_8$ is selected from $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, and —CH$_2$—$C_3$-$C_{10}$ cycloalkyl, wherein $C_3$-$C_{10}$ cycloalkyl is optionally substituted with one, two, or three groups selected from $C_1$-$C_3$ alkyl;

$R_4$ and $R_5$ are independently selected from H and $C_1$-$C_6$ alkyl; or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from N—$C_1$-$C_6$ alkyl, O and S; and wherein the heterocyclyl is optionally substituted with one, two, or three substituents independently selected from halogen, cyano, $C_1$-$C_6$ alkyl, and $C_1$-$C_6$ alkoxy;

$R_6$ is selected from —OH, $C_1$-$C_6$ alkoxy, —OC(O)—$C_1$-$C_6$ alkyl, and —OC(O)phenyl; and $R_7$ is H or $C_1$-$C_6$ alkyl.

In some embodiments, in each of formulae II, IIa, IIb, and IIc, $R_1$ and $R_2$ are H.

In some embodiments, in each of formulae I, IIa, IIb, and IIc, each of $R_1$, $R_2$, $R_4$, and $R_5$ is H.

In some embodiments, in each of formulae II, IIa, IIb, and IIc, $R_6$ is OH.

In some embodiments, in each of formulae II, IIa, IIb, and IIc, $R_7$ is $C_1$-$C_6$ alkyl, such as methyl.

In some embodiments, in each of formulae II, IIa, IIb, and IIc, $R_3$ is OC(O)R$_8$, wherein $R_8$ is $C_1$-$C_6$ alkyl, such as tertiary butyl.

In some embodiments, the compound of formula II is selected from the following compounds:

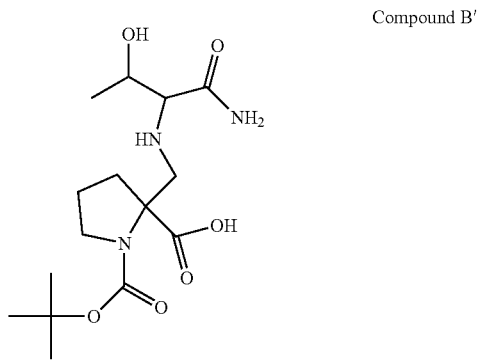

Compound B'

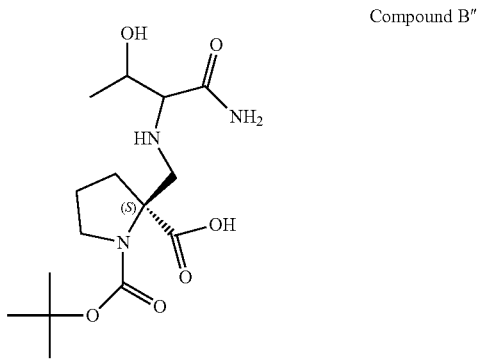

Compound B''

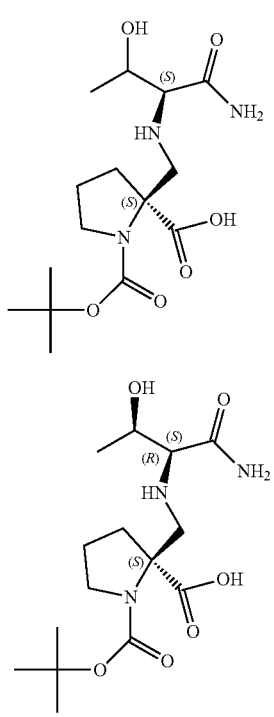

Compound B'''

Compound B

B. Compound of Formula III

In another aspect, provided is a compound of formula III:

formula III wherein:
- $R_b$ is selected from H, halogen, cyano and $C_1$-$C_6$ alkyl;
- $R_1$ is H or $C_1$-$C_6$ alkyl;
- $R_2$ is H or $C_1$-$C_6$ alkyl;
- $R_8$ is selected from $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, and —$CH_2$—$C_3$-$C_{10}$ cycloalkyl, wherein $C_3$-$C_{10}$ cycloalkyl is optionally substituted with one, two, or three groups selected from $C_1$-$C_3$ alkyl;
- $R_4$ and $R_5$ are independently selected from H, $C_1$-$C_6$ alkyl, X, and —$C_1$-$C_6$ alkylene-X, wherein X is selected from:
  - (i) $C_3$-$C_6$ cycloalkyl;
  - (ii) heteroaryl including from 5 to 6 ring atoms wherein one, two, or three of the ring atoms are independently selected from N, NH, N($C_1$-$C_3$ alkyl), O, and S;
  - (iii) heterocyclyl including from three to six ring atoms wherein 1, 2, or 3 of the ring atoms are independently selected from N, NH, N($C_1$-$C_3$ alkyl), O, and S; and
  - (iv) phenyl;
  wherein $C_3$-$C_6$ cycloalkyl, heterocyclyl, heteroaryl, and phenyl are each optionally substituted with one, two, or three substituents independently selected halogen, cyano, $C_1$-$C_6$ alkyl, hydroxyl, and $C_1$-$C_6$ alkoxy;
- or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from N—$C_1$-$C_6$ alkyl, O and S; and wherein the heterocyclyl is optionally substituted with one, two, or three substituents independently selected from halogen, cyano, $C_1$-$C_6$ alkyl, and $C_1$-$C_6$ alkoxy;
- $R_6$ is selected from —OH, $C_1$-$C_6$ alkoxy, —OC(O)—$C_1$-$C_6$ alkyl, and —OC(O)phenyl; and
- $R_7$ is H or $C_1$-$C_6$ alkyl.

In some embodiments, the compound of formula III is a compound of formula IIIa:

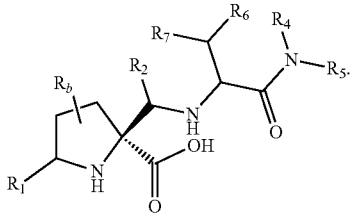

formula IIIa

In some embodiments, the compound of formula IIIa is a compound of formula IIIb:

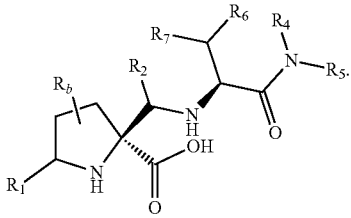

formula IIIb

In some embodiments, the compound of formula IIIb is a compound of formula IIc:

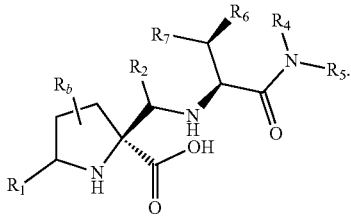

formula IIIc

In some embodiments, in each of formulae II, IIa, IIb, and IIc:
- $R_b$ is selected from H, halogen, cyano and $C_1$-$C_6$ alkyl;
- $R_1$ is H or $C_1$-$C_6$ alkyl;
- $R_2$ is H or $C_1$-$C_6$ alkyl;
- $R_8$ is selected from $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, and —$CH_2$—$C_3$-$C_{10}$ cycloalkyl, wherein $C_3$-$C_{10}$ cycloalkyl is optionally substituted with one, two, or three groups selected from $C_1$-$C_3$ alkyl;

$R_4$ and $R_5$ are independently selected from H and $C_1$-$C_6$ alkyl; or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from N—$C_1$-$C_6$ alkyl, O and S; and wherein the heterocyclyl is optionally substituted with one, two, or three substituents independently selected from halogen, cyano, $C_1$-$C_6$ alkyl, and $C_1$-$C_6$ alkoxy;

$R_6$ is selected from —OH, $C_1$-$C_6$ alkoxy, —OC(O)—$C_1$-$C_6$ alkyl, and —OC(O)phenyl; and $R_7$ is H or $C_1$-$C_6$ alkyl.

In some embodiments, in each of formulae III, IIIa, IIIb, and IIIc, $R_1$ and $R_2$ are H.

In some embodiments, in each of formulae III, IIIa, IIIb, and IIIc, each of $R_1$, $R_2$, $R_4$, and $R_5$ is H.

In some embodiments, in each of formulae III, IIIa, IIIb, and IIIc, $R_6$ is OH.

In some embodiments, in each of formulae III, IIIa, IIIb, and IIIc, $R_7$ is $C_1$-$C_6$ alkyl, such as methyl.

In some embodiments, the compound of formula III is selected from the following compounds:

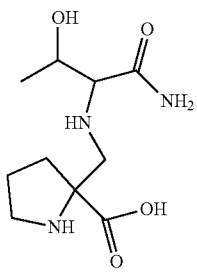

Compound C'

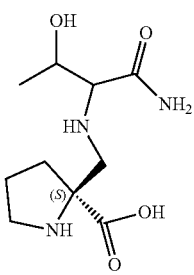

Compound C''

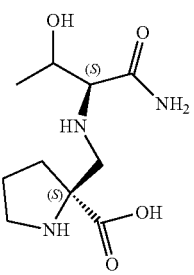

Compound C'''

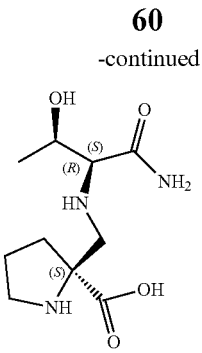

Compound C

C. Compound of Formula IV

In another aspect, provided is a compound of formula IV:

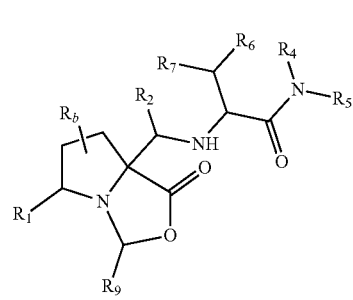

formula IV wherein:

$R_b$ is selected from H, halogen, cyano and $C_1$-$C_6$ alkyl;

$R_1$ is H or $C_1$-$C_6$ alkyl;

$R_2$ is H or $C_1$-$C_6$ alkyl;

$R_4$ and $R_5$ are independently selected from H, $C_1$-$C_6$ alkyl, X, and —$C_1$-$C_6$ alkylene-X, wherein X is selected from
  (i) $C_3$-$C_6$ cycloalkyl;
  (ii) heteroaryl including from 5 to 6 ring atoms wherein one, two, or three of the ring atoms are independently selected from N, NH, N($C_1$-$C_3$ alkyl), O, and S;
  (iii) heterocyclyl including from three to six ring atoms wherein 1, 2, or 3 of the ring atoms are independently selected from N, NH, N($C_1$-$C_3$ alkyl), O, and S; and
  (iv) phenyl;
wherein $C_3$-$C_6$ cycloalkyl, heterocyclyl, heteroaryl, and phenyl are each optionally substituted with one, two, or three substituents independently selected halogen, cyano, $C_1$-$C_6$ alkyl, hydroxyl, and $C_1$-$C_6$ alkoxy;

or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from N—$C_1$-$C_6$ alkyl, O and S; and wherein the heterocyclyl is optionally substituted with one, two, or three substituents independently selected from halogen, cyano, $C_1$-$C_6$ alkyl, and $C_1$-$C_6$ alkoxy;

$R_6$ is selected from —OH, $C_1$-$C_6$ alkoxy, —OC(O)—$C_1$-$C_6$ alkyl, and —OC(O)phenyl; and $R_7$ is H or $C_1$-$C_6$ alkyl; and $R_9$ is —$CCl_3$.

In some embodiments, the compound of formula IV is a compound of formula IVa:

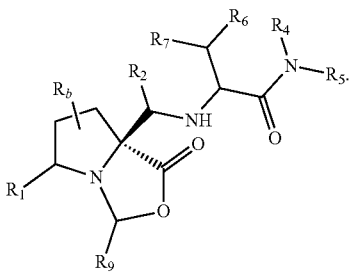

formula IVa

In some embodiments, the compound of formula IVa is a compound of formula IVb:

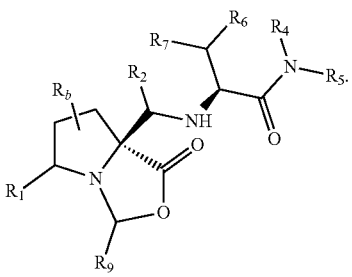

formula IVb

In some embodiments, the compound of formula IVb is a compound of formula IVc:

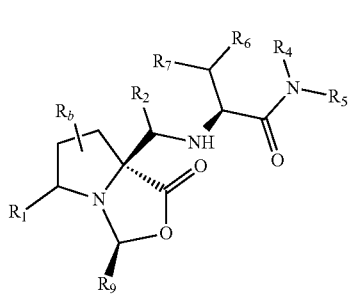

formula IVc

In some embodiments, the compound of formula IVc is a compound of formula IVd:

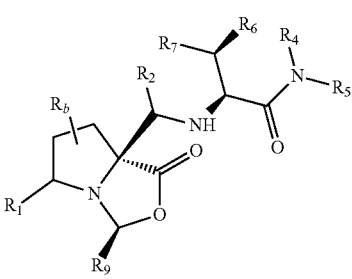

formula IVd

In some embodiments, in each of formulae IV, IVa, IVb, IVc, and IVd:
$R_b$ is selected from H, halogen, cyano and $C_1$-$C_6$ alkyl;
$R_1$ is H or $C_1$-$C_6$ alkyl,
$R_2$ is H or $C_1$-$C_6$ alkyl;

$R_4$ and $R_5$ are independently selected from H and $C_1$-$C_6$ alkyl; or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from —N—$C_1$-$C_6$alkyl, O and S; and wherein the heterocyclyl is optionally substituted with one, two, or three substituents independently selected from halogen, cyano, $C_1$-$C_6$ alkyl, and $C_1$-$C_6$ alkoxy;

$R_6$ is selected from —OH, $C_1$-$C_6$ alkoxy, —OC(O)—$C_1$-$C_6$ alkyl, and —OC(O)phenyl;

$R_7$ is H or $C_1$-$C_6$ alkyl; and $R_9$ is —CCl$_3$.

In some embodiments, in each of formulae IV, IVa, IVb, IVc, and IVd, $R_1$ and $R_2$ are H.

In some embodiments, in each of formulae IV, IVa, IVb, IVc, and IVd, $R_9$ is CCl$_3$.

In some embodiments, in each of formulae IV, IVa, IVb, IVc, and IVd, each of $R_1$, $R_2$, $R_4$, and $R_5$ is H.

In some embodiments, in each of formulae IV, IVa, IVb, IVc, and IVd, $R_6$ is OH.

In some embodiments, in each of formulae IV, IVa, IVb, IVc, and IVd, $R_7$ is $C_1$-$C_6$ alkyl, such as methyl.

In some embodiments, the compound of formula IV is selected from the following compounds:

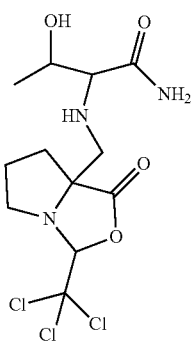

Compound D′

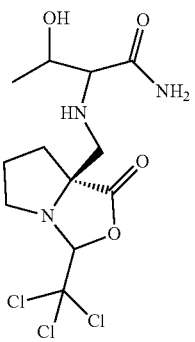

Compound D″

-continued

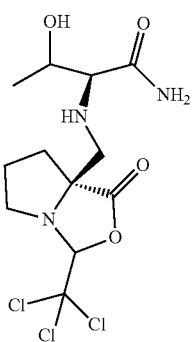
Compound D'''

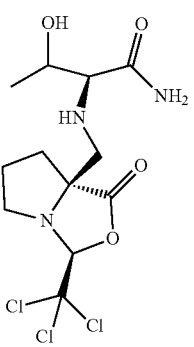
Compound D''''

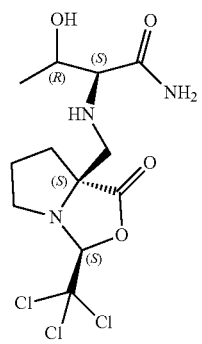
Compound D

D. Compound of Formula V and Compound of Formula VI

In another aspect, provided is a compound of formula V or VI:

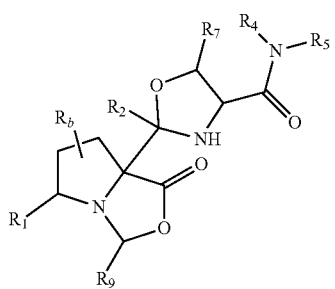
formula V

-continued

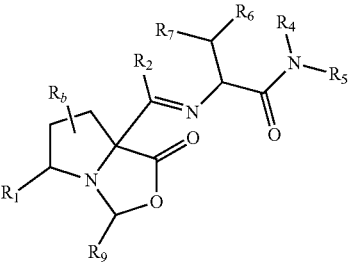
formula VI wherein:

$R_b$ is selected from H, halogen, cyano and $C_1$-$C_6$ alkyl;

$R_1$ is H or $C_1$-$C_6$ alkyl;

$R_2$ is H or $C_1$-$C_6$ alkyl;

$R_4$ and $R_5$ are independently selected from H, $C_1$-$C_6$ alkyl, X, and —$C_1$-$C_6$ alkylene-X, wherein X is selected from:

(i) $C_3$-$C_6$ cycloalkyl;

(ii) heteroaryl including from 5 to 6 ring atoms wherein one, two, or three of the ring atoms are independently selected from N, NH, N($C_1$-$C_3$ alkyl), O, and S;

(iii) heterocyclyl including from three to six ring atoms wherein 1, 2, or 3 of the ring atoms are independently selected from N, NH, N($C_1$-$C_3$ alkyl), O, and S; and (iv) phenyl;

wherein $C_3$-$C_6$ cycloalkyl, heterocyclyl, heteroaryl, and phenyl are each optionally substituted with one, two, or three substituents independently selected halogen, cyano, $C_1$-$C_6$ alkyl, hydroxyl, and $C_1$-$C_6$ alkoxy;

or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from N—$C_1$-$C_6$ alkyl, O and S; and wherein the heterocyclyl is optionally substituted with one, two, or three substituents independently selected from halogen, cyano, $C_1$-$C_6$ alkyl, and $C_1$-$C_6$ alkoxy;

$R_6$ is selected from $C_1$-$C_6$ alkoxy, —OC(O)—$C_1$-$C_6$ alkyl, and —OC(O)phenyl;

$R_7$ is H or $C_1$-$C_6$ alkyl; and $R_9$ is —$CCl_3$.

In some embodiments, the compound of formula V and the compound of formula VI are a compound of formula Va and a compound of formula VIa, respectively:

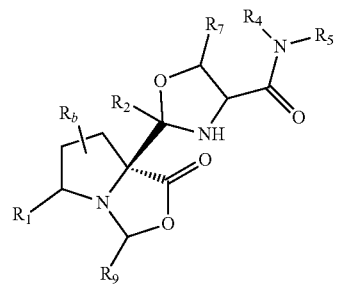
formula Va

-continued

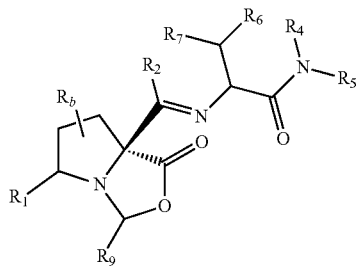

formula VIa

In some embodiments, the compound of formula Va and the compound of formula VIa are a compound of formula Vb and a compound of formula VIb, respectively:

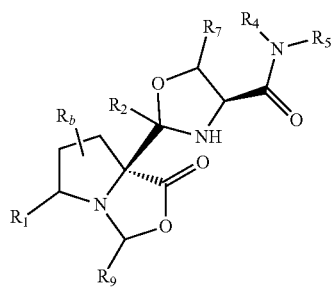

formula Vb

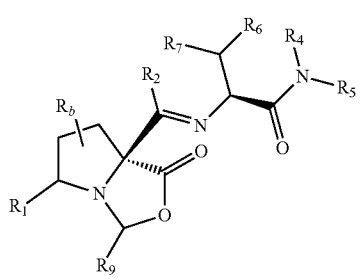

formula VIb

In some embodiments, the compound of formula Vb and the compound of formula VIb are a compound of formula Vc and a compound of formula VIc, respectively:

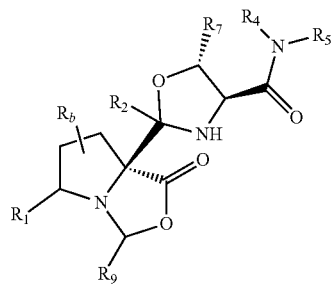

formula Vc

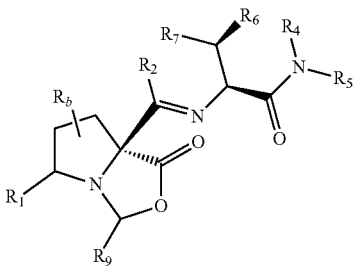

formula VIc

In some embodiments, the compound of formula Vc and the compound of formula VIc are a compound of formula Vd and a compound of VId, respectively:

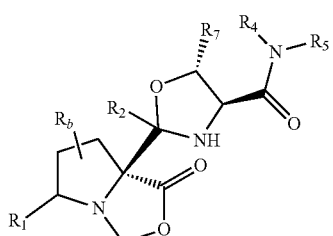

formula Vd

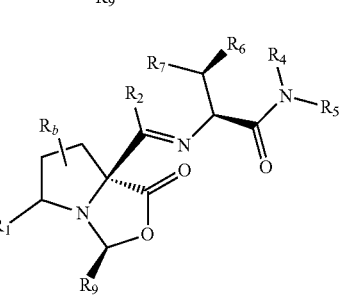

formula VId

In some embodiments, in each of formulae V, Va, Vb, Vc, Vd, VI, VIa, VIb, VIc, and VId:

$R_b$ is selected from H, halogen, cyano and $C_1$-$C_6$ alkyl;
$R_1$ is H or $C_1$-$C_6$ alkyl;
$R_2$ is H or $C_1$-$C_6$ alkyl;
$R_4$ and $R_5$ are independently selected from H and $C_1$-$C_6$ alkyl; or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from N—$C_1$-$C_6$ alkyl, O and S; and wherein the heterocyclyl is optionally substituted with one, two, or three substituents independently selected from halogen, cyano, $C_1$-$C_6$ alkyl, and $C_1$-$C_6$ alkoxy;
$R_6$ is selected from $C_1$-$C_6$ alkoxy, —OC(O)—$C_1$-$C_6$ alkyl, and —OC(O)phenyl;
$R_7$ is H or $C_1$-$C_6$ alkyl; and
$R_9$ is —CCl$_3$.

In some embodiments, in each of formulae V, Va, Vb, Vc, Vd, VI, VIa, VIb, VIc, and VId, $R_1$ and $R_2$ are H.

In some embodiments, in each of formulae V, Va, Vb, Vc, Vd, VI, VIa, VIb, VIc, and VId, and IVd, $R_9$ is CCl3.

In some embodiments, in each of formulae V, Va, Vb, Vc, Vd, VI, VIa, VIb, VIc, and VId, each of $R_1$, $R_2$, $R_4$, and $R_5$ is H.

In some embodiments, in each of formulae V, Va, Vb, Vc, Vd, VI, VIa, VIb, VIc, and VId, $R_6$ is OH.

In some embodiments, in each of formulae V, Va, Vb, Vc, Vd, VI, VIa, VIb, VIc, and VId, $R_7$ is $C_1$-$C_6$ alkyl, such as methyl.

In some embodiments, the compound of formula V is selected from the following compounds:

Compound E'

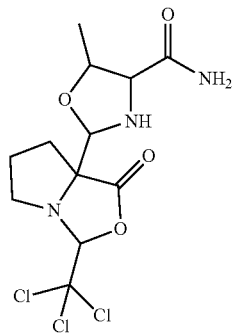

Compound E''

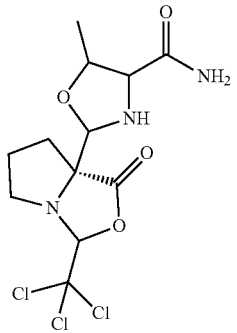

Compound E'''

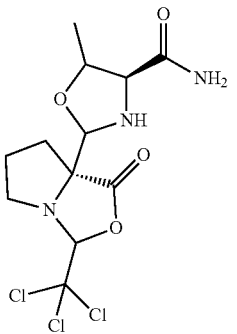

Compound E''''

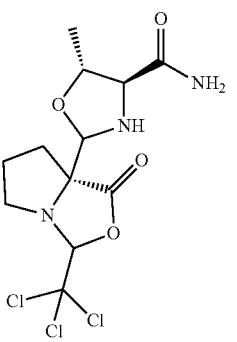

Compound E

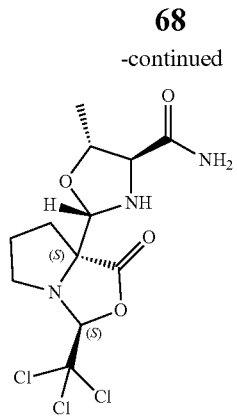

IV Examples

The following examples are illustrative in nature and are in no way intended to be limiting.

Example 1

Preparation of Compound of Formula I

The compound of formula I can be prepared by following the following general scheme:

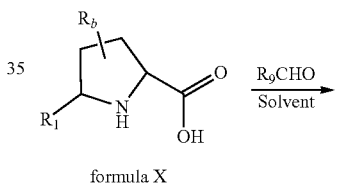

formula X

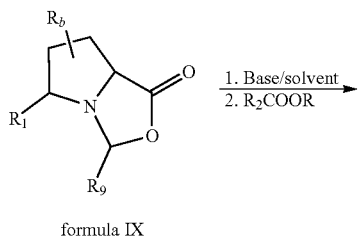

formula IX

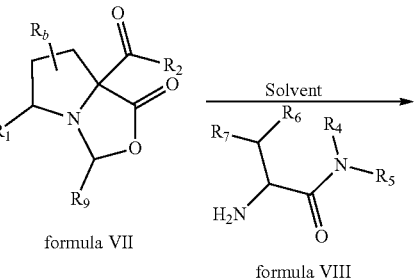

formula VII  formula VIII

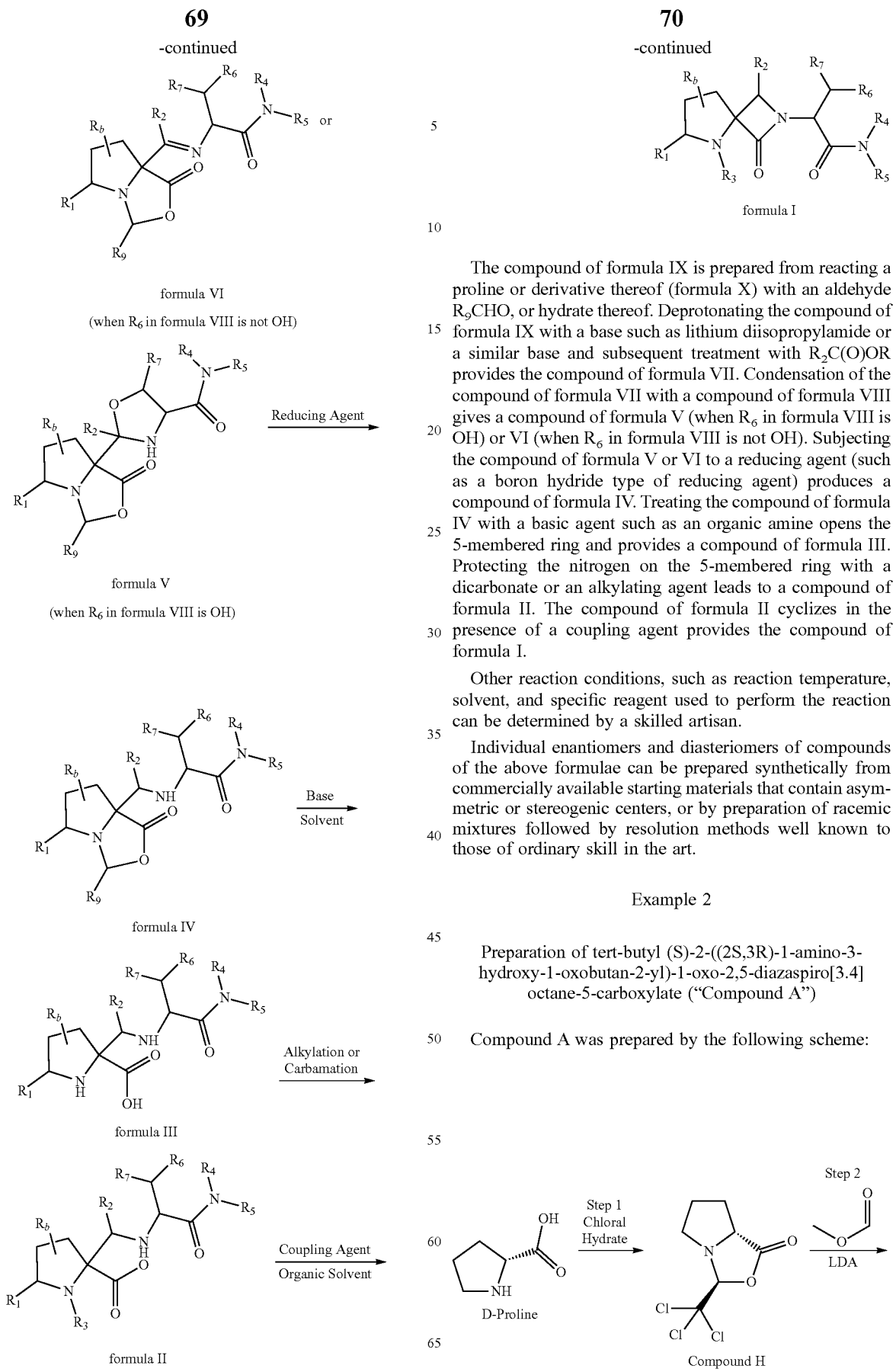

The compound of formula IX is prepared from reacting a proline or derivative thereof (formula X) with an aldehyde $R_9CHO$, or hydrate thereof. Deprotonating the compound of formula IX with a base such as lithium diisopropylamide or a similar base and subsequent treatment with $R_2C(O)OR$ provides the compound of formula VII. Condensation of the compound of formula VII with a compound of formula VIII gives a compound of formula V (when $R_6$ in formula VIII is OH) or VI (when $R_6$ in formula VIII is not OH). Subjecting the compound of formula V or VI to a reducing agent (such as a boron hydride type of reducing agent) produces a compound of formula IV. Treating the compound of formula IV with a basic agent such as an organic amine opens the 5-membered ring and provides a compound of formula III. Protecting the nitrogen on the 5-membered ring with a dicarbonate or an alkylating agent leads to a compound of formula II. The compound of formula II cyclizes in the presence of a coupling agent provides the compound of formula I.

Other reaction conditions, such as reaction temperature, solvent, and specific reagent used to perform the reaction can be determined by a skilled artisan.

Individual enantiomers and diasteriomers of compounds of the above formulae can be prepared synthetically from commercially available starting materials that contain asymmetric or stereogenic centers, or by preparation of racemic mixtures followed by resolution methods well known to those of ordinary skill in the art.

Example 2

Preparation of tert-butyl (S)-2-((2S,3R)-1-amino-3-hydroxy-1-oxobutan-2-yl)-1-oxo-2,5-diazaspiro[3.4]octane-5-carboxylate ("Compound A")

Compound A was prepared by the following scheme:

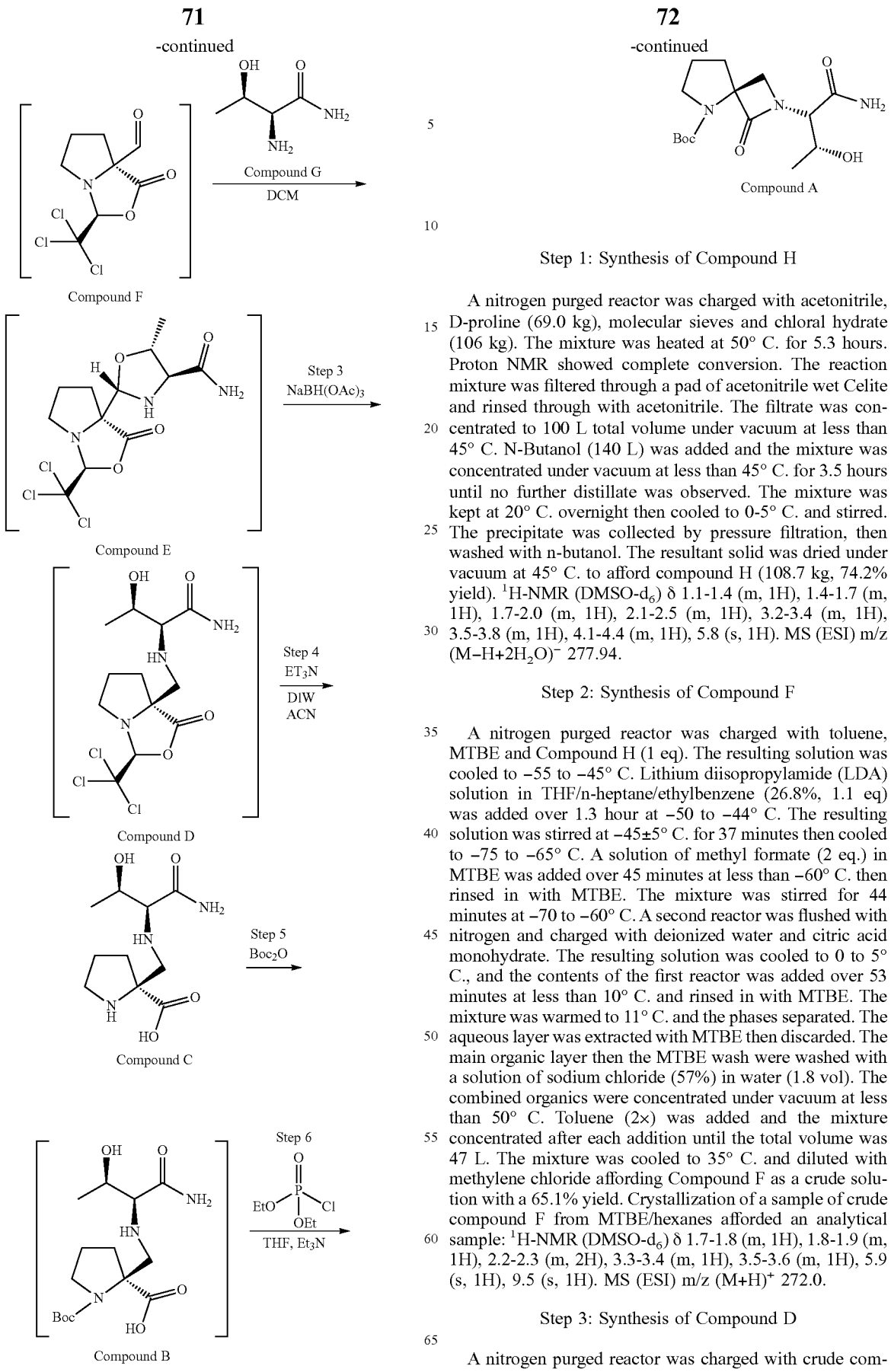

Step 1: Synthesis of Compound H

A nitrogen purged reactor was charged with acetonitrile, D-proline (69.0 kg), molecular sieves and chloral hydrate (106 kg). The mixture was heated at 50° C. for 5.3 hours. Proton NMR showed complete conversion. The reaction mixture was filtered through a pad of acetonitrile wet Celite and rinsed through with acetonitrile. The filtrate was concentrated to 100 L total volume under vacuum at less than 45° C. N-Butanol (140 L) was added and the mixture was concentrated under vacuum at less than 45° C. for 3.5 hours until no further distillate was observed. The mixture was kept at 20° C. overnight then cooled to 0-5° C. and stirred. The precipitate was collected by pressure filtration, then washed with n-butanol. The resultant solid was dried under vacuum at 45° C. to afford compound H (108.7 kg, 74.2% yield). $^1$H-NMR (DMSO-$d_6$) δ 1.1-1.4 (m, 1H), 1.4-1.7 (m, 1H), 1.7-2.0 (m, 1H), 2.1-2.5 (m, 1H), 3.2-3.4 (m, 1H), 3.5-3.8 (m, 1H), 4.1-4.4 (m, 1H), 5.8 (s, 1H). MS (ESI) m/z (M−H+2H$_2$O)$^-$ 277.94.

Step 2: Synthesis of Compound F

A nitrogen purged reactor was charged with toluene, MTBE and Compound H (1 eq). The resulting solution was cooled to −55 to −45° C. Lithium diisopropylamide (LDA) solution in THF/n-heptane/ethylbenzene (26.8%, 1.1 eq) was added over 1.3 hour at −50 to −44° C. The resulting solution was stirred at −45±5° C. for 37 minutes then cooled to −75 to −65° C. A solution of methyl formate (2 eq.) in MTBE was added over 45 minutes at less than −60° C. then rinsed in with MTBE. The mixture was stirred for 44 minutes at −70 to −60° C. A second reactor was flushed with nitrogen and charged with deionized water and citric acid monohydrate. The resulting solution was cooled to 0 to 5° C., and the contents of the first reactor was added over 53 minutes at less than 10° C. and rinsed in with MTBE. The mixture was warmed to 11° C. and the phases separated. The aqueous layer was extracted with MTBE then discarded. The main organic layer then the MTBE wash were washed with a solution of sodium chloride (57%) in water (1.8 vol). The combined organics were concentrated under vacuum at less than 50° C. Toluene (2×) was added and the mixture concentrated after each addition until the total volume was 47 L. The mixture was cooled to 35° C. and diluted with methylene chloride affording Compound F as a crude solution with a 65.1% yield. Crystallization of a sample of crude compound F from MTBE/hexanes afforded an analytical sample: $^1$H-NMR (DMSO-$d_6$) δ 1.7-1.8 (m, 1H), 1.8-1.9 (m, 1H), 2.2-2.3 (m, 2H), 3.3-3.4 (m, 1H), 3.5-3.6 (m, 1H), 5.9 (s, 1H), 9.5 (s, 1H). MS (ESI) m/z (M+H)$^+$ 272.0.

Step 3: Synthesis of Compound D

A nitrogen purged reactor was charged with crude compound F solution, methylene chloride and compound G (1.2 eq). The resulting suspension was heated to 30-35° C. for 6 hours then stirred overnight at 20-25° C. to Compound E. An analytical sample of compound E was isolated via silica gel column chromatography (methylene chloride/ethyl acetate eluent) followed by crystallization from ethyl acetate/hexanes. $^1$H-NMR (DMSO-d$_6$) δ 1.2 (d, 3H, J=8 Hz), 1.8-1.9 (m, 2H), 2.0-2.1 (m, 1H), 2.2-2.3 (m, 1H), 3.1-3.2 (m, 1H), 3.2-3.3 (m, 1H), 3.6-3.8 (m, 2H), 4.7 (d, 2H, J=15 Hz), 5.5 (s, 1H), 7.2 (s, 1H), 7.5 (s, 1H). MS (ESI) m/z (M+H)$^+$ 372.0.

The crude compound E mixture was cooled to 20° C. and sodium triacetoxyborohydride (3.0 eq) was added over 1.5 H at 20-29° C. then the mixture was stirred 5 hours at 30-35° C. Water was added at 15-20° C. over 49 min with gas evolution. The media was stirred then the phases separated. The aqueous layer was extracted twice with methylene chloride (2 x). The combined organics were washed with saturated aqueous sodium bicarbonate. The methylene chloride extracts assayed by HPLC as containing pure compound D with a 78.9% yield. An analytical sample of compound D was crystallized from toluene/hexane and water. $^1$H-NMR (DMSO-d$_6$) δ 1.1 (d, 3H, J=8 Hz), 1.8-1.9 (m, 2H), 2.0-2.1 (m, 2H), 2.7-2.8 (m, 2H), 3.1-3.2 (m, 1H), 3.3-3.4 (m, 1H), 3.6-3.7 (m, 1H), 4.7 (d, 2H, J=6 Hz), 5.6 (s, 1H), 7.0 (s, 1H), 7.1 (s, 1H). MS (ESI) m/z (M+H) 374.1.

Step 4: Synthesis of Compound C

The crude solution of Compound D was concentrated under vacuum at less than 45° C. to a total volume of 110 L. Acetonitrile was added and the mixture concentrated to a total volume of 110 L. Acetonitrile, water and triethylamine (6 eq) were added and the mixture heated to 45° C. then stirred f. The mixture was concentrated under vacuum at less than 50° C. to a total volume of less than 110 L. Acetonitrile then Isopropanol were added. The mixture was cooled to 15-20° C., MTBE was added over 1 hour at 15-20° C. and the resultant slurry was stirred at 15-20° C. and the product collected by filtration. The crude solids were slurried in methanol and stirred at 60-65° C. then the suspension was slowly cooled to 20-25° C. The product was collected by filtration and washed with methanol and the solids dried under vacuum at 50° C. to give Compound C with a 72.4% yield. $^1$H-NMR (MeOH-d$_4$) δ 1.23 (3H, d, J=6.4 Hz); 1.9-2.1 (m, 3H), 2.2-2.3 (m, 1H), 2.9 (d, 1H, J=13 Hz), 3.0 (d, 1H, J=6 Hz), 3.1 (d, 1H, J=13 Hz), 3.2-3.3 (m, 1H), 3.4-3.5 (m, 1H), 3.8 (pentet, 1H, J=6 Hz). MS (ESI) m/z (M+H)$^+$ 246.2.

Step 5: Synthesis of Compound B

To a nitrogen purged reactor was charged sequentially acetone, water and Compound C (1 eq). Triethylamine (6 eq) was added to the media in 20 minutes at less than 30° C. and rinsed in with acetone. A solution of di-tert-butyl dicarbonate (1.3 eq) in was added to the mixture at less than 30° C. and rinsed in with acetone (13 L). The mixture was stirred at 20-30° C. n. A solution of di-tert-butyl dicarbonate (0.5 eq) in acetone was added to the mixture. A solution of di-tert-butyl dicarbonate (0.5 eq) in acetone was added. The mixture was concentrated at atmospheric pressure to 65 L total volume. Acetone then THF were added and the mixture concentrated to 65 L total volume. The resulting suspension was cooled to 0-5° C. then the precipitate collected by filtration and washed with THF and dried under vacuum at 45° C. to afford Compound B with a 90.5% yield. $^1$H-NMR (DMSO-d$_6$) δ 1.1 (d, 3H, J=6 Hz), 1.3 (s, 5H), 1.4 (s, 4H), 1.7-1.8 (m, 2H), 1.9-2.0 (m, 1H), 2.2-2.4 (m, 1H), 2.5-3.1 (m, 3H), 3.2-3.5 (m, 3H), 3.6-3.7 (m, 1H), 7.2 (d, 1H, J=16 Hz), 7.4, (d, 1H, J=16 Hz). MS (ESI) m/z (M+H)$^+$ 346.3.

Step 6: Synthesis of Compound A

To a nitrogen purged reactor was charged THF and Compound B (1 eq). Triethylamine (1.8 eq) was added at 20-25° C. and rinsed in with THF. A solution of diethylchlorophosphate (1.8 eq) in THF was added at 20-33° C. After stirring at 25-33° C., a solution of sodium chloride in water was added at 25-30° C. and the phases separated. The aqueous layer was extracted twice with ethyl acetate. The combined organics were concentrated under vacuum at less than 60° C. to a total volume of 65 to 70 L. Ethyl acetate was added and the mixture concentrated to 65 to 70 L total volume. Ethyl acetate followed by a solution of sodium chloride in water (60 L) were added to the mixture. Phosphoric acid was then added to adjust the pH to 2.0. The mixture was stirred at 20-25° C. and the phases separated and the aqueous discarded. The organic layer was washed with a mixture of sodium chloride and aqueous ammonia and the wash back extracted with ethyl acetate. The combined organics were mixed with activated charcoal and stirred overnight then filtered through ethyl acetate wet Celite and rinsed through with ethyl acetate). The filtrate was concentrated under vacuum at less than 60° C. to a total volume of 100 L. Ethyl acetate was added and the mixture concentrated to 100 L after each addition. Ethyl acetate was added and the mixture was cooled to 20-25° C. The mixture was heated to 45-55° C. and the residual solids removed by filtration, washed with ethyl acetate and discarded.

The filtrate was concentrated under vacuum at less than 60° C. to a total volume of 105 L. The mixture was heated to 65-70° C. then cooled to 25° C. Diisopropyl ether was added and the mixture stirred at 20-25° C. The precipitate was collected by filtration and washed with diisopropyl ether then dried at 50° C. to give Compound A as a white crystalline powder with 67.2% yield. $^1$H-NMR (DMSO-d$_6$) δ 1.1 (m, 3H), 1.3 (s, 4H), 1.4 (s, 5H), 1.7-1.9 (m, 2H), 2.0-2.3 (m, 2H), 3.1-3.5 (m, 3H), 3.5-4.0 (m, 3H), 4.9 (m, 1H), 7.1-7.6 (m, 2H). MS (ESI) m/z (M+Na)$^+$ 350.2.

Throughout this specification reference is made to publications such as US and foreign patent applications, journal articles, book chapters, and others. All such publications are expressly incorporated by reference in their entirety, including supplemental/supporting information sections published with the corresponding references, for all purposes unless otherwise indicated.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A process of producing a compound of formula I or a pharmaceutically acceptable salt thereof, comprising contacting a compound of formula II with a coupling agent in an organic solvent to obtain a compound of formula I or a pharmaceutically acceptable salt thereof:

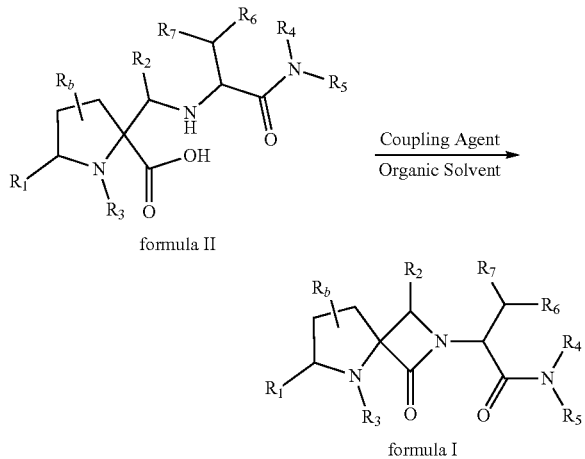

formula II formula I wherein:
- $R_b$ is selected from H, halogen, cyano and $C_1$-$C_6$ alkyl;
- $R_1$ is H or $C_1$-$C_6$ alkyl;
- $R_2$ is H or $C_1$-$C_6$ alkyl;
- $R_3$ is selected from $C_1$-$C_6$ alkyl and C(O)OR$_8$;
- $R_8$ is selected from $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, and —CH$_2$—$C_3$-$C_{10}$ cycloalkyl, wherein $C_3$-$C_{10}$ cycloalkyl is optionally substituted with one, two, or three groups selected from $C_1$-$C_3$ alkyl;
- $R_4$ and $R_5$ are independently selected from H, $C_1$-$C_6$ alkyl, X, and $C_1$-$C_6$ alkylene-X, wherein X is selected from:
  - (i) $C_3$-$C_6$ cycloalkyl;
  - (ii) heteroaryl including from 5 to 6 ring atoms wherein one, two, or three of the ring atoms are independently selected from N, NH, N($C_1$-$C_3$ alkyl), O, and S;
  - (iii) heterocyclyl including from three to six ring atoms wherein 1, 2, or 3 of the ring atoms are independently selected from N, NH, N($C_1$-$C_3$alkyl), O, and S; and
  - (iv) phenyl;
  - wherein $C_3$-$C_6$ cycloalkyl, heterocyclyl, heteroaryl, and phenyl are each optionally substituted with one, two, or three substituents independently selected halogen, cyano, $C_1$-$C_6$ alkyl, hydroxyl, and $C_1$-$C_6$ alkoxy:
- or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from N—$C_1$-$C_6$ alkyl, O and S; and wherein the heterocyclyl is optionally substituted with one, two, or three substituents independently selected from halogen, cyano, $C_1$-$C_6$ alkyl, and $C_1$-$C_6$ alkoxy;
- $R_6$ is selected from —OH, $C_1$-$C_6$ alkoxy, —OC(O)—$C_1$-$C_6$ alkyl, and —OC(O)phenyl; and
- $R_7$ is H or $C_1$-$C_6$ alkyl.

2. The process of claim 1, wherein the coupling agent comprises at least one selected from (Benzotriazol-1-yloxy)tris(dimethylamino)phosphonium hexafluorophosphate (BOP), (Benzotriazol-1-yloxy)tripyrrolidinophosphonium hexafluorophosphate (PyBOP), (7-Azabenzotriazol-1-yloxy)tripyrrolidinophosphonium hexafluorophosphate (PyAOP), Bromotripyrrolidinophosphonium hexafluorophosphate (PyBrOP), Bis(2-oxo-3-oxazolidinyl)phosphinic chloride (BOP—Cl), O-(Benzotriazol-1-yl)-N,N,N',N'-tetramethyluronium hexafluorophosphate (HBTU), O-(Benzotriazol-1-yl)-N,N,N',N'-tetramethyluronium tetrafluoroborate (TBTU), O-(7-Azabenzotriazol-1-yl)-N,N,N',N'-tetramethyluronium hexafluorophosphate (HATU), O-(7-Azabenzotriazol-1-yl)-N,N,N',N'-tetramethyluronium tetrafluoroborate (TATU), O-(6-Chlorobenzotriazol-1-yl)-N,N,N',N'-tetramethyluronium hexafluorophosphate (HCTU), O-[(Ethoxycarbonyl)cyanomethylenamino]-N,N,N',N'-tetra methyluronium tetrafluoroborate (TOTU), (1-Cyano-2-ethoxy-2-oxoethylidenaminooxy)dimethylamino-morpholino-carbenium hexafluorophosphate (COMU), O—(N-Suc-cinimidyl)-1,1,3,3-tetramethyl-uronium tetrafluoroborate (TSTU), O-(5-Norbornene-2,3-dicarboximido)-N,N,N',N'-tetramethyluronium tetrafluoroborate (TNTU), O-(1,2-Dihydro-2-oxo-1-pyridyl-N,N,N',N'-tetramethyluronium tetrafluoroborate (TPTU), N,N,N',N'-Tetramethyl-O-(3,4-dihydro-4-oxo-1,2,3-benzotriazin-3-yl) uranium tetrafluoroborate (TDBTU), N,N,N',N'-Tetramethylchloroformamidinium Hexafluorophosphate (TCFH), 3-(Diethylphosphoryloxy)-1,2,3-benzotriazin-4 (3H)-one (DEPBT), and Carbonyldiimidazole (CDI).

3. The process of claim 1, wherein the coupling agent comprises a carbodiimide optionally together with 1-hydroxybenzotriazole (HOBt) and the carbodiimide selected from dicyclohexylcarbodiimide (DCC), diisopropylcarbodiimide (DIC), and ethyl-(N',N'-dimethylamino) propylcarbodiimide hydrochloride (EDC).

4. The process of claim 1, wherein the coupling agent comprises a di-$C_1$-$C_6$ alkyl halophosphate, a dialkyl phosphinic halide, or propanephosphonic acid anhydride.

5. The process of claim 4, wherein the coupling agent comprises diethyl chlorophosphite.

6. The process of claim 1, wherein the coupling agent is used together with an organic base, the organic base comprising an amine.

7. The process of claim 6, wherein the amine is triethyl amine, N,N-Diisopropylethylamine (DIPEA), or 4-Dimethylaminopyridine (DMAP).

8. The process of claim 1, wherein the organic solvent comprises dimethylformamide (DMF), dimethyl sulfoxide (DMSO), N-Methyl-2-pyrrolidone (NMP), acetonitrile (MeCN), dichloromethane (DCM), tetrahydrofuran (THF), or 2-methyltetrahydrofuran (2-MeTHF).

9. The process of claim 1, further comprising contacting a compound of formula IV with a base in a solvent to obtain a compound of formula III, wherein the compound of formula III is subsequently contacted with an alkylating agent or carbamating agent to obtain a compound of formula II, wherein Rb, $R_1$, $R_2$, $R_3$, $R_4$, $R_5$, $R_6$, and $R_7$ are the same as described in claims 1, and $R_9$ is —CCl$_3$:

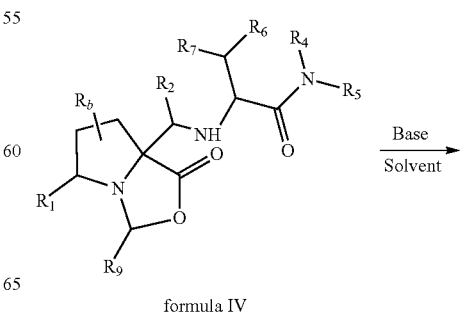

formula IV

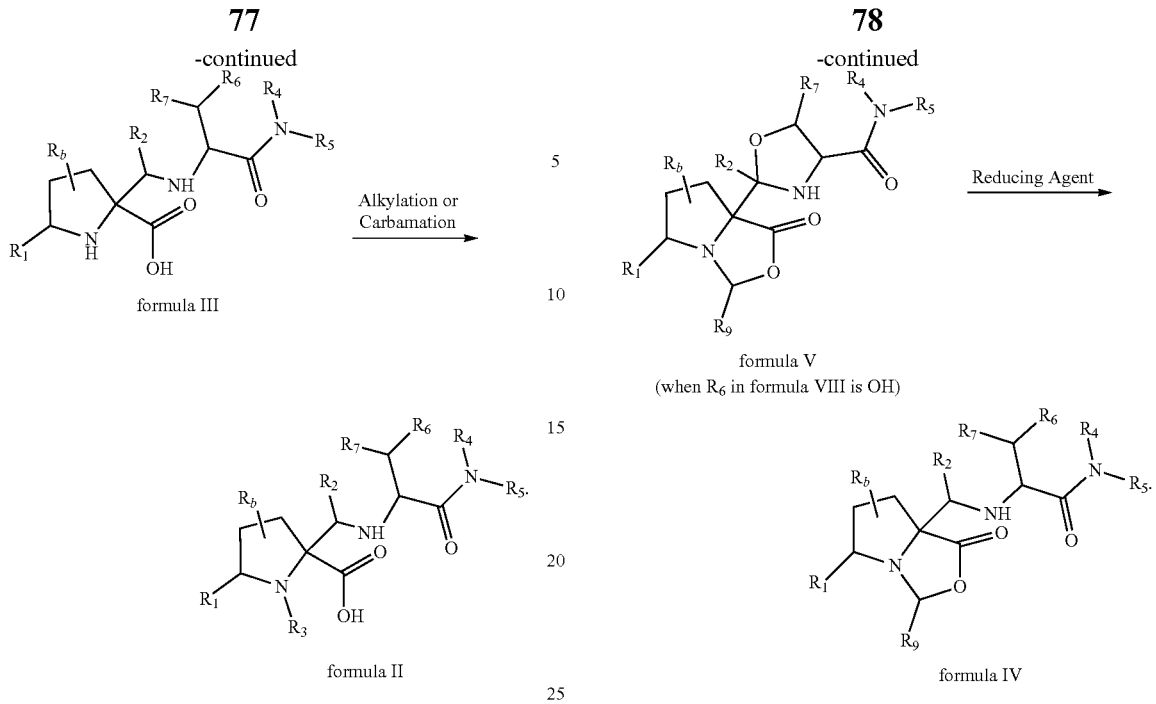

formula III formula II formula VII formula VI
(when R6 in formula VIII is not OH)   or

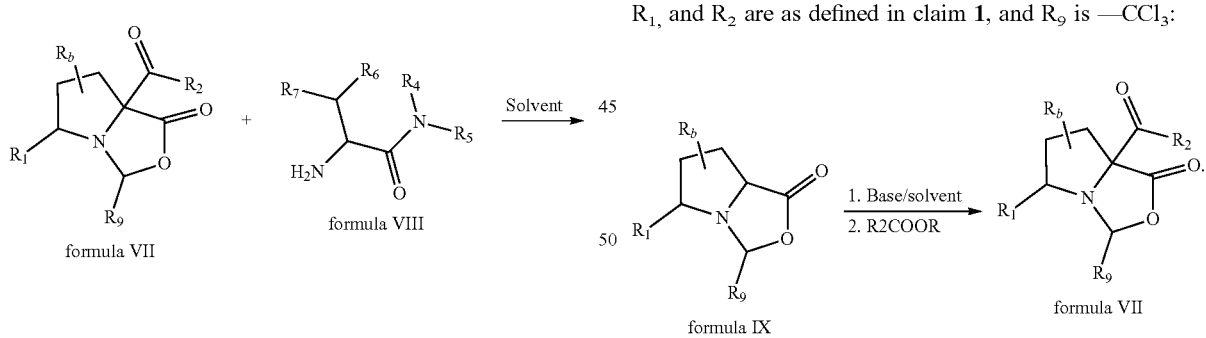

formula V
(when R6 in formula VIII is OH)

formula IV formula VIII formula IX formula VII

10. The process of claim 9, wherein the base comprises an amine, the solvent is an aqueous solvent, the alkylating agent is $C_1$-$C_6$ alkyl-halide, and the carbamating agent is di-$R_8$-dicarbonate.

11. The process of claim 9, further comprising contacting a compound of formula VII with an amine of formula VIII to obtain a condensed product of formula V or VI, which is subsequently contacted with a reducing agent to obtain a compound of formula IV, wherein Rb, $R_1$, $R_2$, $R_3$, $R_4$, $R_5$, $R_6$, and $R_7$ are as defined in claims 1, and $R_9$ is —$CCl_3$.

12. The process of claim 11, wherein the solvent for the condensation reaction comprises dichloromethane, dimethylformamide, tetrahydrofuran, acetonitrile, or toluene.

13. The process of claim 11, wherein the reducing agent comprises a boron hydride selected from sodium borohydride, lithium borohydride, calcium borohydride, magnesium borohydride, sodium triacetoxyborohydride ($NaBH(OAc)_3$), $NBu_4BH_4$, $NaCNBH_3$, and $NMe_4BH(OAc)_3$.

14. The process of claim 11, further comprising contacting a compound of formula IX with a base to deprotonate the a carbon next to a carbonyl (CO) in a solvent, which is subsequently followed by addition of $R_2COOR$ to obtain the compound of formula VII, wherein R is methyl or ethyl, $R_b$, $R_1$, and $R_2$ are as defined in claim 1, and $R_9$ is —$CCl_3$:

15. The process of claim 14, wherein the deprotonation is conducted at a temperature of −80 to −20° C., the base comprises lithium diisopropylamide, and the solvent comprises toluene optionally mixed with methyl tert-butyl ether (MTBE), THF optionally mixed with toluene or MTBE, or 2-MeTHF optionally mixed with toluene or MTBE.

16. The process of claim 14, further comprising contacting a compound of formula X with an aldehyde $R_9CHO$, or hydrate thereof, to obtain a compound of formula IX, wherein $R_b$ and $R_1$ are as defined in claims 1, and $R_9$ is —$CCl_3$:

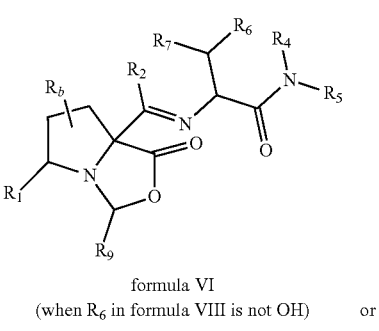

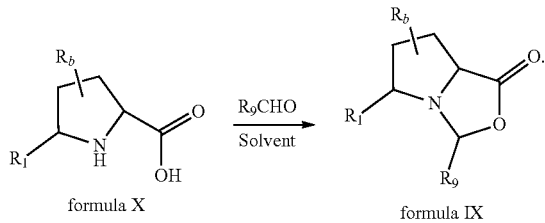

17. The process of claim 16, wherein the solvent used to obtain the compound of formula IX comprises THF, acetonitrile, or toluene.

18. The process of claim 1, wherein:
$R_b$ is selected from H, halogen, cyano and $C_1$-$C_6$ alkyl;
$R_1$ is H or $C_1$-$C_6$ alkyl;
$R_2$ is H or $C_1$-$C_6$ alkyl;
$R_3$ is selected from $C_1$-$C_6$ alkyl and C (O) $OR_8$;
$R_8$ is selected from $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, and —$CH_2$—$C_3$—$C_{10}$ cycloalkyl, wherein $C_3$-$C_{10}$ cycloalkyl is optionally substituted with one, two, or three groups selected from $C_1$-$C_3$ alkyl;
$R_4$ and $R_5$ are independently selected from H and $C_1$-$C_6$ alkyl; or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from N—$C_1$-$C_6$ alkyl, O and S; and wherein the heterocyclyl is optionally substituted with one, two, or three substituents independently selected from halogen, cyano, $C_1$-$C_6$ alkyl, and $C_1$-$C_6$ alkoxy;
$R_6$ is selected from —OH, $C_1$-$C_6$ alkoxy, —OC(O)—$C_1$-$C_6$ alkyl, and —OC(O) phenyl; and
$R_7$ is H or $C_1$-$C_6$ alkyl.

19. A compound of formula II:

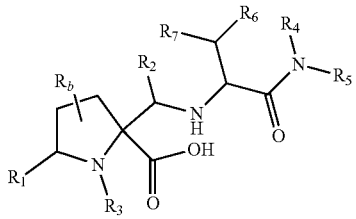

wherein:
$R_b$ is selected from H, halogen, cyano and $C_1$-$C_6$ alkyl;
$R_1$ is H or $C_1$-$C_6$ alkyl;
$R_2$ is H or $C_1$-$C_6$ alkyl;
$R_3$ is selected from $C_1$-$C_6$ alkyl and C(O)$OR_8$;
$R_8$ is selected from $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, and —CH2—$C_3$—$C_{10}$ cycloalkyl, wherein $C_3$-$C_{10}$ cycloalkyl is optionally substituted with one, two, or three groups selected from $C_1$-$C_3$ alkyl;
$R_4$ and $R_5$ are independently selected from H, $C_1$-$C_6$ alkyl, X, and —$C_1$-$C_6$ alkylene-X, wherein X is selected from
(i) C3-C6 cycloalkyl;
(ii) heteroaryl including from 5 to 6 ring atoms wherein one, two, or three of the ring atoms are independently selected from N, NH, N ($C_1$-$C_3$ alkyl), O, and S;
(iii) heterocyclyl including from three to six ring atoms wherein 1, 2, or 3 of the ring atoms are independently selected from N, NH, N ($C_1$-$C_3$ alkyl), O, and S; and
(iv) phenyl;
wherein $C_3$-$C_6$ cycloalkyl, heterocyclyl, heteroaryl, and phenyl are each optionally substituted with one, two, or three substituents independently selected halogen, cyano, $C_1$-$C_6$ alkyl, hydroxyl, and $C_1$-$C_6$ alkoxy;
or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from N—$C_1$-$C_6$ alkyl, O and S; and wherein the heterocyclyl is optionally substituted with one, two, or three substituents independently selected from halogen, cyano, $C_1$-$C_6$ alkyl, and $C_1$-$C_6$ alkoxy;
$R_6$ is selected from—OH, $C_1$-$C_6$ alkoxy, —OC(O) —$C_1$-$C_6$ alkyl, and —OC(O) phenyl; and
$R_7$ is H or $C_1$-$C_6$ alkyl.

20. A compound of formule III.

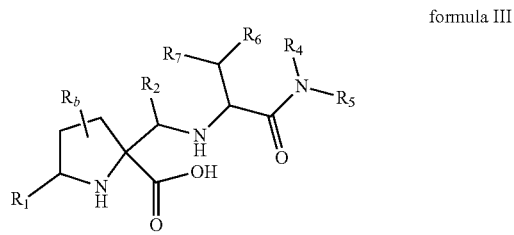

wherein:
$R_b$ is selected from H, halogen, cyano and $C_1$-$C_6$ alkyl;
$R_1$ is H or $C_1$-$C_6$ alkyl;
$R_2$ is H or $C_1$-$C_6$ alkyl;
$R_8$ is selected from $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, and —$CH_2$-$C_3$-$C_{10}$ cycloalkyl, wherein $C_3$-$C_{10}$ cycloalkyl is optionally substituted with one, two, or three groups selected from C1-C3 alkyl;
$R_4$ and $R_5$ are independently selected from H, $C_1$-$C_6$ alkyl, X, and —$C_1$-$C_6$ alkylene-X, wherein X is selected from
(i) C3-C6 cycloalkyl;
(ii) heteroaryl including from 5 to 6 ring atoms wherein one, two, or three of the ring atoms are independently selected from N, NH, N ($C_1$-$C_3$ alkyl), O, and S;
(iii) heterocyclyl including from three to six ring atoms wherein 1, 2, or 3 of the ring atoms are independently selected from N, NH, N ($C_1$-$C_3$ alkyl), O, and S; and
(iv) phenyl;
wherein $C_3$-$C_6$ cycloalkyl, heterocyclyl, heteroaryl, and phenyl are each optionally substituted with one, two, or three substituents independently selected halogen, cyano, $C_1$-$C_6$ alkyl, hydroxyl, and $C_1$-$C_6$ alkoxy;
or $R_4$ and $R_5$ together with the nitrogen to which they are attached form heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from N—$C_1$-$C_6$ alkyl, O and S; and wherein the heterocyclyl is optionally substituted with one, two, or three substituents independently selected from halogen, cyano, $C_1$-$C_6$ alkyl, and $C_1$-$C_6$ alkoxy;

$R_6$ is selected from -OH, $C_1$-$C_6$ alkoxy, —OC(O)—$C_1$-$C_6$ alkyl, and —OC(O) phenyl; and $R_7$ is H or $C_1$-$C_6$ alkyl.

* * * * *